United States Patent [19]

Wittwer et al.

[11] Patent Number: 4,738,724

[45] Date of Patent: Apr. 19, 1988

[54] METHOD FOR FORMING PHARMACEUTICAL CAPSULES FROM STARCH COMPOSITIONS

[75] Inventors: Fritz Wittwer, Lupsingen; Ivan Tomka, Lenzburg; Hans-Ulrich Bodenmann, Münchenstein; Thomas Raible, Jona, all of Switzerland; Louis S. Gillow, Rockaway, N.J.

[73] Assignee: Warner-Lambert Company, Morris Plains, N.J.

[21] Appl. No.: 909,525

[22] Filed: Sep. 19, 1986

Related U.S. Application Data

[63] Continuation-in-part of Ser. No. 796,517, Nov. 8, 1985, Pat. No. 4,673,438, Ser. No. 798,344, Nov. 8, 1985, abandoned, Ser. No. 641,550, Aug. 17, 1984, abandoned, Ser. No. 641,663, Aug. 17, 1984, abandoned, and Ser. No. 641,664, Aug. 17, 1984, abandoned, said Ser. No. 796,517, is a continuation of Ser. No. 579,318, Feb. 13, 1984, abandoned, which is a continuation-in-part of Ser. No. 467,982, Feb. 18, 1983, abandoned, said Ser. No. 798,344, is a continuation of Ser. No. 951,577, Dec. 20, 1982, abandoned, said Ser. No. 641,550, is a continuation-in-part of Ser. No. 543,694, Oct. 20, 1983, abandoned, said Ser. No. 641,663, is a continuation-in-part of Ser. No. 557,306, Dec. 2, 1983, Pat. No. 4,576,284, Ser. No. 557,502, Dec. 2, 1983, abandoned, Ser. No. 557,500, Dec. 2, 1983, Ser. No. 593,692, Oct. 20, 1983, Ser. No. 543,698, Oct. 20, 1983, abandoned, and Ser. No. 543,699, Oct. 20, 1983, abandoned, said Ser. No. 641,664, is a continuation-in-part of Ser. No. 548,794, Nov. 4, 1983, abandoned.

[51] Int. Cl.$^4$ .................. C08C 3/00; B29C 45/00
[52] U.S. Cl. ................... 106/213; 106/126; 106/214; 264/328.1; 264/328.14; 264/328.15; 264/328.18
[58] Field of Search .......... 264/328 B, 328.14, 328.15, 264/328.18, 328.1; 206/530, 531, 532; 106/213

[56] References Cited

U.S. PATENT DOCUMENTS

| | | | |
|---|---|---|---|
| 2,831,852 | 4/1958 | Savage | 536/91 |
| 3,664,495 | 5/1972 | Graham | 206/530 |
| 4,076,846 | 2/1978 | Nakatsuka et al. | 426/89 |
| 4,482,386 | 11/1984 | Wittwer et al. | 106/213 |
| 4,576,284 | 3/1986 | Wittwer et al. | 206/530 |

Primary Examiner—Theodore Morris
Attorney, Agent, or Firm—Howard Olevsky; Stephen Raines

[57] ABSTRACT

Novel injection molded pharmaceutical capsules of starch having a cap member, a body member, means to form a plurality of compartments therein; and means for locking the cap and body members together to form a tamper-resistant connection.

6 Claims, 38 Drawing Sheets

FIG. 4
FIG. 5
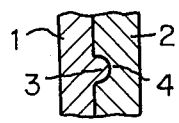
FIG. 6
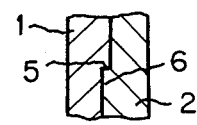
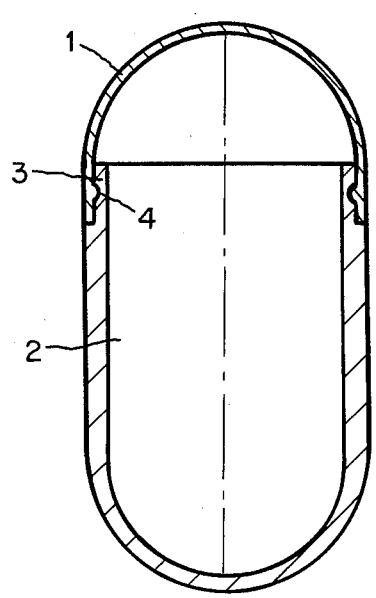
FIG. 7
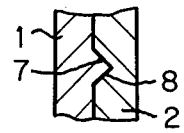
FIG. 8
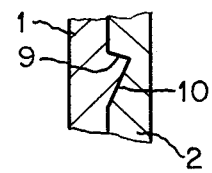
FIG. 9
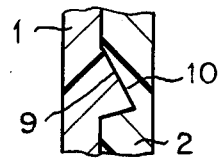
FIG. 11
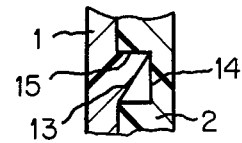
FIG. 13
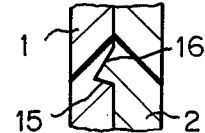
FIG. 10
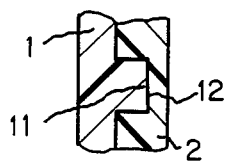
FIG. 12
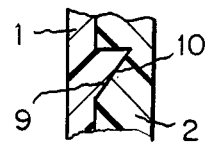
FIG. 14
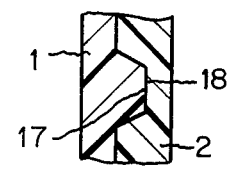

FIG. 72
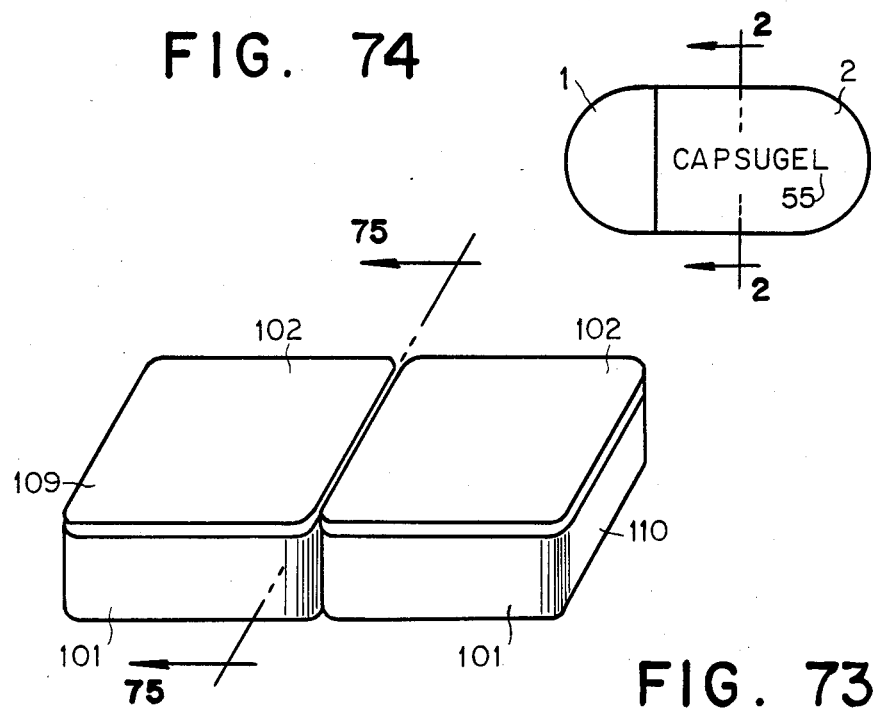
FIG. 74
FIG. 73
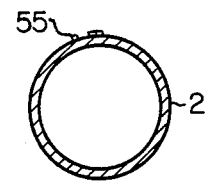
FIG. 75
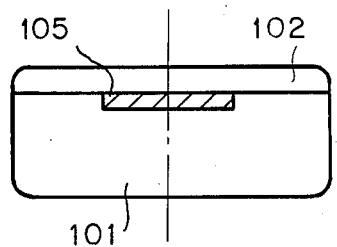

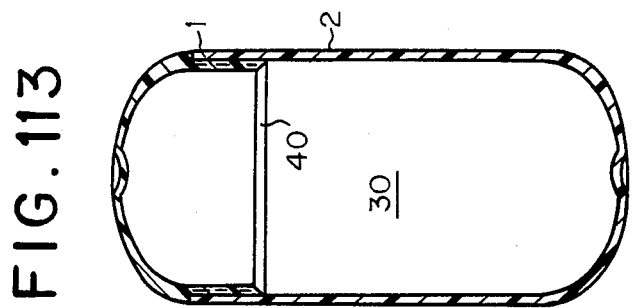
FIG. 113
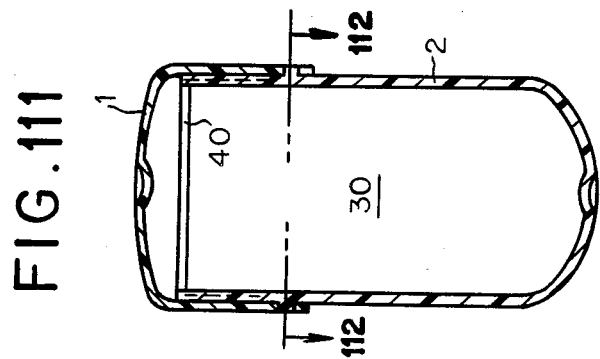
FIG. 111
FIG. 112
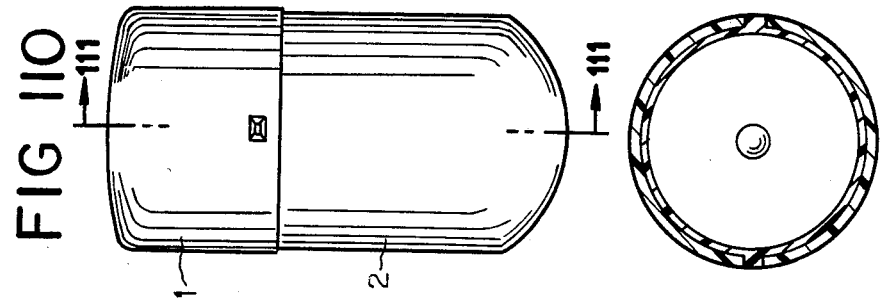
FIG. 110
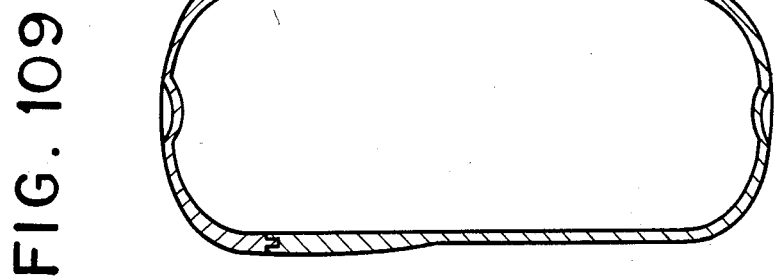
FIG. 109

METHOD FOR FORMING PHARMACEUTICAL CAPSULES FROM STARCH COMPOSITIONS

CROSS REFERENCE TO RELATED APPLICATIONS

This application is a continuation-in-part of each of the following applications:

U.S. Ser. No. 796,517, filed Nov. 8, 1985, now U.S. Pat. No. 4,673,438 which is a continuation of U.S. Ser. No. 579,318, now abandoned, filed Feb. 13, 1984, which is a continuation-in-part of U.S. Ser. No. 467,982, filed Feb. 18, 1983 now abandoned;

U.S. Ser. No. 641,550, filed Aug. 17, 1984 now abandoned, which is a continuation-in-part of U.S. Ser. No. 543,694, filed Oct. 20, 1983 now abandoned;

U.S. Ser. No. 641,663, filed Aug. 17, 1984 now abandoned, which is a continuation-in-part of U.S. Ser. No. 557,306, filed Dec. 2, 1983, now U.S. Pat. No. 4,576,284, U.S. Ser. No. 557,502, filed Dec. 2, 1983 now abandoned, U.S. Ser. No. 557,500, filed Dec. 2, 1983, U.S. Ser. No. 543,692, filed Oct. 20, 1983, U.S. Ser. No. 543,698, filed Oct. 20, 1983 now abandoned and U.S. Ser. No. 543,699, filed Oct. 20, 1983 now abandoned;

U.S. Ser. No. 641,664, filed Aug. 17, 1984 now abandoned, which is a continuation-in-part of U.S. Ser. No. 548,794, filed Nov. 4, 1983 now abandoned; and U.S. design patent application Ser. No. 798,344 filed Nov. 8, 1985 now abandoned, is a continuation of U.S. Ser. No. 451,577, filed Dec. 20, 1982, abandoned.

FIELD OF THE INVENTION

The present invention relates to useful molded products, especially pharmaceutical capsules prepared by the injection molding of various starch compositions. The invention particularly concerns injection molded capsules containing one or a plurality of compartments for different dosage forms and having locking means to provide a tamper resistant seal between the cap and body members of the capsule.

BACKGROUND OF INVENTION

Capsule-making machines have been developed to utilize dip-molding technology. Such technology involves the dipping of capsule-shaped pins into a gelatin solution, removing the pins from the solution, drying the gelatin on the pins, stripping off the gelatin capsule parts from the pins, adjusting for length, cutting, joining and ejecting the capsules. Prior art capsule-making machines have utilized a combination of mechanical and pneumatic elements to perform these functions in a dip-molding technique. While these apparatus are, in general, suitable for the intended purpose, it is desirable to produce capsules by injection molding them while at the same time precisely controlling the properties of the gelatin in order to produce the capsules hygienically and with minimum dimensional deviations so that the capsules can be filled on high speed equipment.

A prerequisite for any material to be moldable by an injection process is its ability to pass a glass transition point at a temperature compatible with the thermal stability of the material and the technical possibilities of an injection molding device. A further prerequisite to the use of any material for delivering shaped products of high dimensional stability in an injection molding process is a high minimum elastic recovery after the mold is opened. This parameter can be adjusted by manipulating the dispersity of the material at the molecular level during the injection process.

The following patents disclose suitable compounds or mixtures which can be injection molded into various articles.

Shirai et al., in U.S. Pat. No. 4,216,240, describes an injection molding process which produces an oriented fibrous protein product. To obtain a flowable mass for the molding process, the protein mixtures used by Shirai et al. have to be denatured and thus lose their capacity to undergo dissolution.

Nakatsuka et al., in U.S. Pat. No. 4,076,846, uses binary mixtures of starch with salts of protein materials to obtain an edible shaped article by an injection molding process.

Heusdens et al., in U.S. Pat. No. 3,911,159, discloses the formation of filamentous protein structures which produce edible products.

The use of an injection molding device for producing capsules of starch, however, is new and has not been previously suggested in the technical literature.

SUMMARY OF THE INVENTION

The invention relates to useful molded products, especially pharmaceutical capsules, prepared by the injection molding of various starch compositions. The invention additionally concerns capsules containing a plurality of compartments for different dosage forms and having various locking means to provide a tamper resistant seal between the cap and body portions of the capsule.

One embodiment of the present invention is an injection molded pharmaceutical capsule for the dosage of solid creamy or liquid medicaments, exhibiting an essentially amorphous polymer structure and comprising a cap member and a body member, each having at least one open end, and sidewall means; means located in each sidewall means for connecting the cap and body members together, wherein the connecting means are configured and arranged to face each other in order to achieve after connection of the cap and body members, a separation resistant connection; and said capsule molded from a starch having a molecular mass range of between about 10,000 and 20,000,000 Daltons and a water content of between about 5 and 30 weight percent. The water content of the starch may range from 15 to 22.5 percent by weight, preferably between about 15 and 19 percent by weight. The completed injection molded capsule exhibits a self-sustaining shape and negligible reversible elastic deformation of the starch. The capsule may further contain means, such as internal partitions, for forming two or more compartments in the interior spaces defined by the body and cap members.

In a further embodiment of the capsules of the invention, the ratio of the outside diameter of the cap member may be equal to or greater than the overall length of the capsule. Also, the outer surface of the capsule, in the area where the cap and body members are joined together, may be substantially smooth. In capsules having such a configuration, each sidewall is cylindrical and axially joined to the other. In addition, the open end of the cap or body member includes a recessed annular shoulder for receiving the compartment forming means. The depth of this recessed annular shoulder is substantially equal to the thickness of the sidewall means of the cap or body member which does not include this shoulder. Preferably, the open end of each of the cap and body members includes a recessed annular shoulder for receiving compartment forming means.

In another embodiment of the invention, the connecting means is at least one locking means comprising at least one continuous or discontinuous annular ridge located on the sidewall means of either the cap or body member and an annular groove located on the other member. The dimensions of the ridge and groove are preferably substantially equal. Further, each of the sidewall means is structurally and dimensionally adapted so that the ridge cooperates with the groove to form, as noted above, an interlocked capsule when the cap and body members are brought together.

In an alternate embodiment, the sidewall means of the cap and body members each have an open and a closed end. Further, the inner surface of the cap member is located at or below the level of a plane perpendicular to the open end of the sidewall means of the body member such that, after filling the body member with medicaments and closing the capsule, substantially no air is entrapped between the inner surface of the cap member and the medicaments.

In a further embodiment of such a capsule, the cap member is a circular disc which is coaxially joined with the open end of the body member by placing the plane surface of the circular disc in circumferential engagement with the annular periphery of the open end of the body member. Additionally, the cap member may possess an annular recess located at its circumferential edge facing the open end of the body member wherein the sidewall means of the body member mates with and protrudes into this recess.

The cap member may be die-molded directly onto the open end of the body member to serve as stopper means after the body member has been filled with medicaments, to seal the medicaments within the capsule. Further, the cap and body members may be die-molded so as to be joinable in a distinctive shape to facilitate the visual and palpable identification of the capsule In various alternate embodiments of the invention, some combination of letters and/or numbers may be embossed or debossed upon the surface of the capsule in order to aid in the identification thereof. Further, the seal between the cap member and body member of such capsules may be rendered liquid-proof by wetting the joining surfaces of each member prior to the joining of said members.

Advantageously, the invention provides means for forming two or more compartments in the interior spaces defined by the body and cap members wherein the ratio of the outside diameter of the cap member is equal to or greater than the overall length of the capsule. Preferably, the cap and body members each have an open end and a closed end. The cap member is configured and dimensioned as a closure for the open end of the body member and is directly connected to the body member after the body member has been filled with medicaments so as to retain these medicaments within the capsule. Cover means, such as a circular disc, may be inserted into the open end of the body member after the body member has been filled and before the cap member is connected to it.

By utilizing an alternate construction for these capsules, one may prepare a divisible pharmaceutical capsule dosage form comprising a plurality of connected molded capsules as described above. In this construction, the means for forming two or more compartments comprises a connection which is integrally molded with the body or cap member, or both. This connection is breakable so as to separate the capsule into subunits for administration of the appropriate pharmaceutical dosage.

For capsules of the type described above, one of the cap and body members may be a blister sheet while the other member is a blister cover sheet attached to the blister sheet. In this configuration, the means for connection may comprise lamella means for connecting two individual body or cap member combinations. Further, the compartment forming means may comprise one or a plurality of internal partitions which are integrally molded with the cap and/or body members.

In an embodiment of the pharmaceutical capsule described herein, one or both of the body and cap members may include at least one integrally molded internal partition oriented parallel to the open end and perpendicular to the sidewall of the member. In an alternate arrangement, at least one integrally molded internal partition is oriented perpendicular to the open end and parallel to the sidewall of the member. Additionally, the open end of the body or cap members, or both, may include closure means which form a closed compartment for retaining different medicaments in each compartment.

Advantageously, the starch composition comprises amylose, amylopectin or mixtures thereof, and may additionally include, for example, up to 40 weight percent of a low molecular weight organic plasticizer compound, up to 10 weight percent of one or more lubricants of a lipid; a saturated or unsaturated plant fatty acid or corresponding salt; a stearate; talc; a silicone; or mixture thereof, as well as up to 10 weight percent of a dyestuff, pigment, coloring agent or mixture thereof. The most preferred starch for use in the invention comprises either potato starch or corn starch. These starch compositions may be used to form, by injection molding, any of the previously described pharmaceutical capsules.

The present invention also discloses a method for making these molded pharmaceutical capsules. This method comprises maintaining the starch composition unde predetermined controlled conditions of temperature and pressure; plasticizing the composition in extruder means at a temperature above its glass transition point and a pressure between about $6 \times 10^7$ N/m$^2$ and $3 \times 10^8$ N/,$^2$ with optionally up to 40% of a low molecular weight organic plasticizer compound preferably between about 0.5 to 10 weight percent; injecting a portion of the plasticized composition from the extruder into mold means at an elevated pressure to shape the capsule members; cooling the capsule members and ejecting the capsule members from the mold means wherein the injection molded capsule exhibits a self sustaining shape and negligible elastic deformation of the starch.

The composition is preferably molded at a temperature below about 80° C. In addition, the compound may initially be plasticized at a temperature of between about 80°–240° C., preferabl between about 110° C. and 180° C. This method optionally contemplates the addition of at least one of a lubricant, a dyestuff, a pigment, a coloring agent or mixtures thereof to the starch before molding.

Those skilled in art will be able to form starch capsules by die-molding, i.e. profile extrusion, compression molding, vacuum forming, thermal forming, extrusion molding or polymer casting in combination with vacuum forming. The most preferred method, however, is injection-molding.

BRIEF DESCRIPTION OF THE DRAWINGS

Further benefits and advantages of the invention will become apparent from a consideration of the following description given with reference to the accompanying drawing figures which specify and show preferred embodiments of the present invention.

FIG. 4 is a cross-sectional view of another capsule of the invention;

FIGS. 5 to 14 are partial cross-sectional views showing further embodiments of capsule locking mechanisms according to the invention;

FIG. 72 is a side elevated view of a capsule embodiment having the name of the vendor embossed thereon;

FIG. 73 is a sectional view of FIG. 72 taken along line 73—73;

FIG. 74 is a perspective view of a divisible capsule consisting of two subunits;

FIG. 75 is a cross-sectional view of FIG. 74 taken along line 75—75;

FIGS. 106-109 are cross-sectional views showing four alternate embodiments of locking means for capsules of the present invention;

FIG. 110 is a top plan view of another capsule having locking means;

FIG. 111 is a cross-sectional view of the capsule of FIG. 110 taken along line 111—111;

FIG. 112 is a cross-sectional view of the capsule of FIG. 111 taken along line 112—112;

FIG. 113 is a cross-sectional view of the locking means of another capsule;

FIG. 118A is a schematic showing a combined injection molding device-microprocessor apparatus for making capsule parts;

DETAILED DESCRIPTION OF THE PREFERRED EMBODIMENTS

Figure 1:
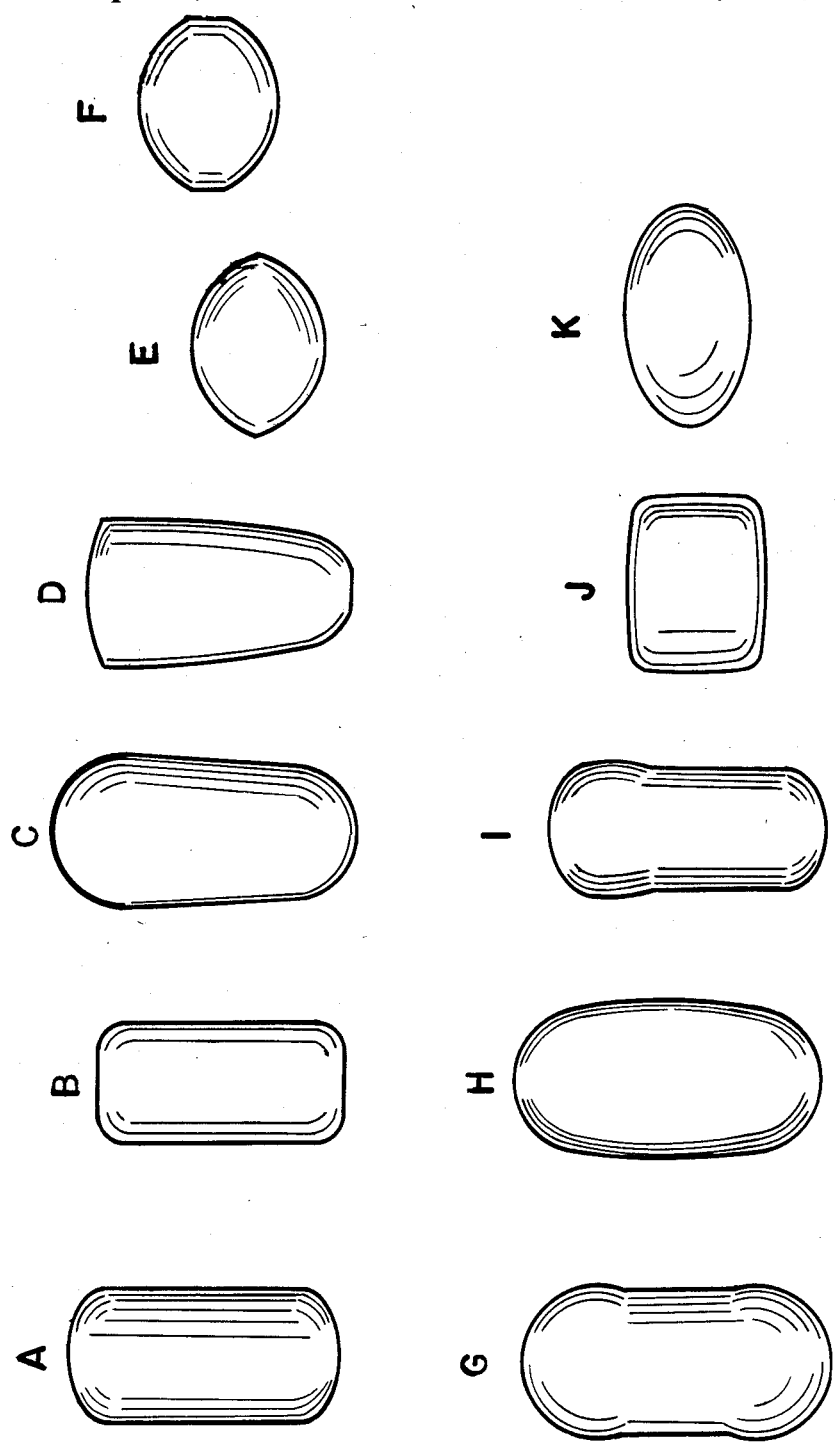
FIGS. 1 (A-K) are top plan views showing eleven embodiments for the outward appearance of capsules constructed according to the present invention.

When in the following description the term "starch" is used, this also includes foams, modifications or derivatives of starch as well as combinations thereof with other hydrophilic polymers whose properties are acceptable for the injection molding of capsules. Starch made from corn, wheat, potatoes, rice, tapioca and the like, having a molecular mass range of 10,000 to 20,000,000 Daltons, is preferred. The starch also has a water content of 5-30%, preferably of 15-25% and especially of 17-20%.

The starch advantageously contains about 0 to 100% of amylose, and about 100 to 0% of amylo-pectin; preferably 0 to 70% of amylose, and about 95 to 10% of amylo-pectin and is most preferably potato starch and maize (i.e., corn) starch.

These starches are hydrophilic polymers with molecular masses from approximately $10^4$ to $2 \times 10^7$ Dalton carrying molecular groups in their backbone and/or in their side chains and capable of forming and/or participating in hydrogen bridges. Such hydrophilic polymers exhibit in their water adsorption isotherm (in the temperature range between approximately 0° to 200° C.) an inflection point close to the water activity point at 0.5.

Hydrophilic polymers are distinguished from the group called hydrocolloids by their molecular dispersity of said hydrophilic polymers a fraction of water—according to the working range of the present invention—of 5 to 30% by weight of said hydrophilic poymers must be included provided that the temperature of said hydrophilic polymers is in the working range of between 80° and 240° C. of the present invention.

While the preferred embodiment of the injection molding apparatus of the invention is for the method of producing starch capsules from various types of starch, it has been found that quality capsules may also be manufactured utilizing the present invention with starch modified by the addition of:

(a) crosslinking agents such as: epichlorohydrin, anhydride of dicarboxylic acid, formaldehyde, phosphorous oxychlorine, metaphosphate, acrolein, organic divinylsulfones and the like;

(b) crosslinking the starch with microwaves and the like;

(c) prior processing treatment with acids and/or enzymes in order to yield dextrines and/or pregelatinizing and/or treatment with ultrasonic and/or treatment with gamma radiation.

(d) chemical derivatives such as: oxidized starch, monophosphate, starch diphosphate, starch acetate, starch sulfate, starch hydroxyethylether, carboxymethyl starch, starch ether, 2-hydroxypropyl starch, alphabetized starch, starch xanthide, starch chloracetic acid, starch ester, formaldehyde starch, sodium carboxymethyl starch; and (e) mixtures or combinations of these modified starches and starch modification procedures described in sections (a) to (d) respectively.

In addition it has been found that the injection molding apparatus of the present invention can produce quality capsules with various types of starch and/or with the above mentioned modified starches (a), (b), (c), (d) and (e) combined with extenders such as sunflower proteins, soybean proteins, cotton seed proteins, peanut proteins, blood proteins, egg proteins, rape seed proteins and acetylated derivatives thereof, gelatin, crosslinked gelatin, vinylacetate, polysaccharides such as cellulose, methylcellulose, hydroxypropyl cellulose, hydroxypropyl-methylcellulose, hydroxymethyl-cellulose, hydroxyethylcellulose, sodium carboxy methylcellulose, polyvinyl-pyrrolidone, bentonite, agar-agar, gum arabic, guar, dextran, chitin, polymaltose, polyfructose, pectin, alginates, alginic acids and the like, monosaccharides such as glucose, fructose, saccharose and the like, oligosaccharides such as lactose and the like, silicates, carbonates and bicarbonates.

The quantity of extender is controlled so as not to affect the ability of the starch to be injection molded. In addition it has been found that the injection molding apparatus of the present invention can produce capsules having enteric properties (2 hours resistant in gastric juice, well soluble within 30 minutes in intestinal juice according to USP XX) with various types of starch and/or with the above mentioned modified starches A, B, C, D and E combined with enteric polymers such as hydroxypropyl-methylcellulose phtalate (HPMCP), cellulose acetylphtalate (CAP), acrylates and methacrylates, polyvinyl-acetate-phtalate (PVAP), phtalated gelatin, succinated gelatin, crotonic acid, shellac and the like.

For the manufacture of capsules with different types of starches and/or modified starches and/or extended starches as mentioned above, the utilization of plasticizers, lubricants and coloring agents specifically of pharmaceutical grades leads to optimal product qualities. These may include:

Pharmacologically acceptable plasticizers, such as polyethylene glycol or, preferably, low-molecular weight organic plasticizers, such as glycerol, sorbitol, dioctyl-sodium sulfocsuccinate, triethyl citrate, tributyl citrate, 1, 2-propylenglycol, mono-, di-, and tri-acetates of glycerol etc., utilized at various concentrations of about 0.5–40% preferably at 0.5–10% based upon the weight of the starch composition;

Pharmacologically acceptable lubricants, such as lipids, i.e. glycerides (oils and fats), wax and phospholipids, such as unsaturated and saturated plant fatty acids and salts thereof, such as the stearates of aluminum, calcium, magnesium and tin; as well as talc, silicones, etc. are used at concentrations of about 0.001–10% based upon the weight of the starch composition;

Pharmaceutically acceptable coloring agents, such as azo-dyes and other dyestuffs and pigments as iron oxides, titanium dioxides, natural dyes etc. used at concentrations of about 0.001–10% preferably at 0.001–5% based upon the weight of the starch composition.

Figure 2:
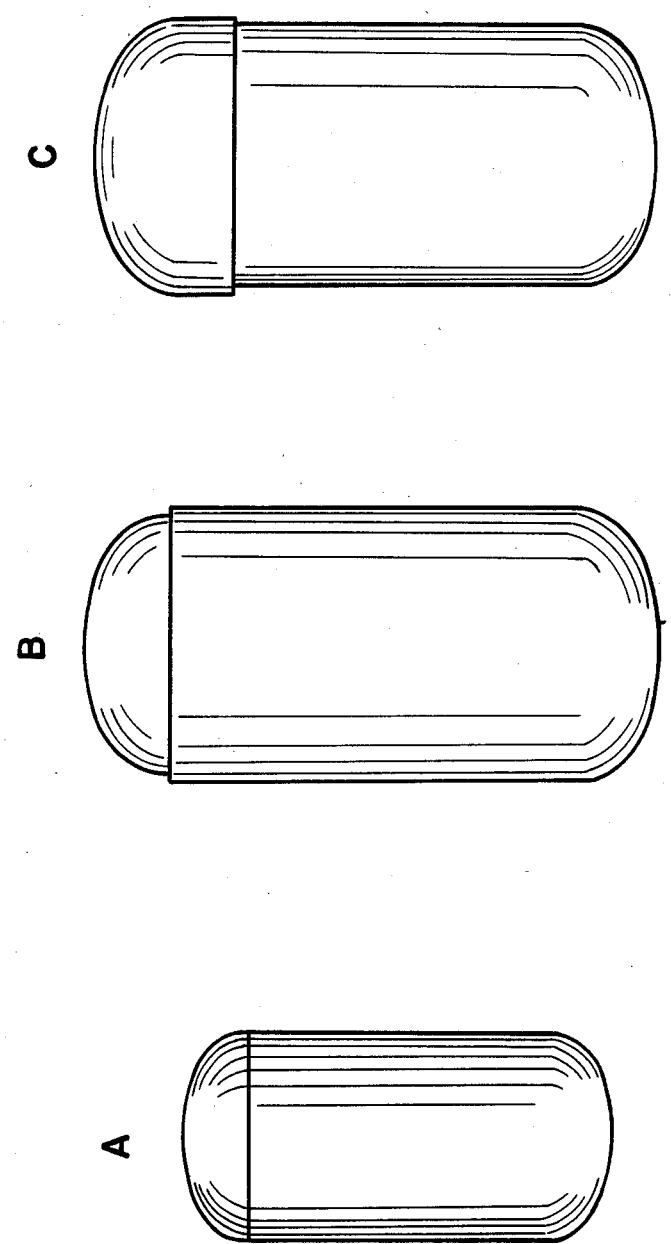
FIGS. 2 (A-C) are top plan views of three embodiments for joining the cap and body members of these capsules.

Referring now to FIGS. 1 (A–K), there are illustrated eleven alternate embodiments for the external appearance of the capsule of the present invention. While one skilled in the art may be able to suggest a number of additional capsule shapes embodying applicants' invention, those depicted herein are illustrated as representative of several classes of such distinctive outward appearance. FIGS. 2 (A–C) illustrates three basic embodiments into which the outward appearance of the capsule produced by applicants' invention may be classified. FIG. 2A depicts a capsule having a cap 1 and a body 2 of equivalent width. In FIG. 2B, the cap 1 is narrower than body 2, while in FIG. 2C, the cap 1 is wider than body 2.

Figure 3:
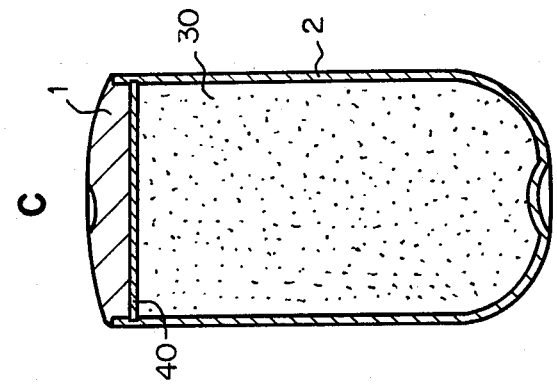
FIGS. 3 (A-C) are three sectional views of alternate locking arrangements for the capsule of FIG. 1(D)
Figure 3:
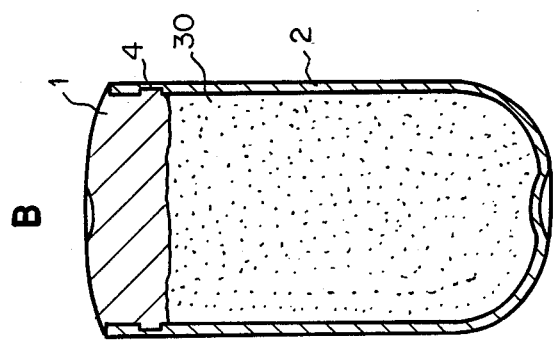
Figure 3:
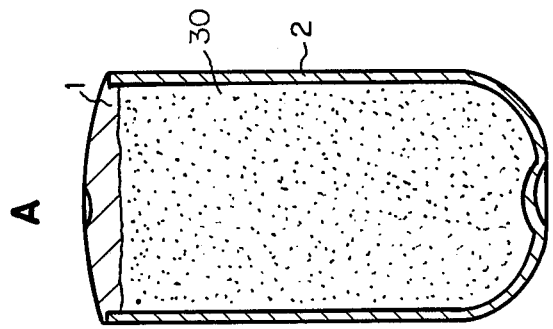

In FIG. 3A there is shown an embodiment of a capsule which may be filled with a medicinal pharmaceutical to be swallowed by a patient. In this embodiment the cap 1 is formed by die-molding so as to provide a smooth outer surface when joined, i.e. it has the same diameter as the capsule body 2 which is filled with the contents 30.

FIG. 3B shows another embodiment wherein body 2 is provided with groove 4 to maintain a tight seal with cap 1 when the parts are joined.

In FIG. 3C there is shown a further embodiment wherein a flat, circular plate or disc 40 is inserted into body 2 so as to completely cover filling material 30. In this embodiment, cap 1 is formed by die-molding so as to provide a smooth outer surface when joined, i.e., it has the same outer diameter as the body 2 which is filled with the medicinal contents 30. The cover plate 40 will permit injection molding of the cap at a very high speed.

Due to manufacturing limitations imposed by current dip-molding processes, capsules produced thereby have a disadvantage in that they do not have secure locking means to prevent separation after filling and joining. There is a problem if such a capsule, especially one containing food or drugs, can be opened or tampered with.

The present invention provides for molding high precision locking articles, especially capsules which are liquid- and tamper-proof. In this application a "locking capsule" is defined to include a filled and joined capsule wherein the capsule parts are formed so as to impede separation or tampering with the contents.

The capsule shown in FIG. 4 has a cap 1 and a body 2. The cap 1 has an annular ridge 3 protruding from the inner surface of the side wall adjacent to the open end of the body 2. Ridge 3 mates with a recessed annular groove 4 of the body 2. The ridge 3 and groove 4 are structurally and dimensionally adapted so that they are interlocked by a snap-in action when the capsule parts are joined. It is to be understood that:

the ridge 3 may be a continuous ring or it may constitute a number of segments or cams cooperating with a continuous or discontinuous groove;

the locking means may comprise one or more ridge and groove structures; and/or the cross-sectional shape of the locking means may comprise not only semicircular forms but any other suitable form such as a triangle, a semi-oval or other fractions of circles, ovals, rectangles, squares, triangles or other polygonal shapes.

FIGS. 5 to 14 are alternate embodiments of the capsule shown in FIG. 4. In FIG. 5, the cap 1 has a semicircular groove 3 which mates with a complimentary ridge 4 of body 2. In FIG. 6, the cap 1 has a right angle groove 5 which mates with a right angle ridge 6 of body 2. FIG. 7 shows a further embodiment wherein the cap 1 has an annular conical ridge 7 which mates and locks with an annular conical groove 8 on body 2.

FIG. 8 shows another capsule wherein the cap 1 has an annular triangular ridge 9 which mates and locks with a corresponding annular triangular groove 10 on body 2. It has been found that the optimum locking force occurs when the short side of the triangular ridge 9 faces the open end of the other part. For better locking, therefore, the short side of the triangular ridge 9 faces the short side of the triangular groove 10. The joining of the capsule parts is facilitated when the shortest side of the triangular ridge facing the open end of the other capsule part forms with the adjacent side wall an angle of about 134 to 190 degrees.

FIG. 9 shows another cap 1 having a t riangular ridge 9 for mating in locking engagement with a triangular groove 10 on body 2.

FIG. 10 shows a cap 1 having an annular rectangular ring 11 in mating and locking engagement with a corresponding annular rectangular groove 12 on body 2.

FIG. 11 shows a cap 1 having annular ridge with a triangular cross section 13 wherein the shortest face of the triangle 15 mates and locks with the top surface of a rectangular groove 14 in body 2.

FIG. 12 shows another embodiment of a cap 1 having a triangular ridge 9 in mating configuration with a triangular groove 10 on body 2.

FIG. 13 shows a cap 1 having a ridge 15 with a bead-like cross sectional area in mating and locking engagement with a corresponding annular groove 16 of a corresponding cross sectional area on body 2.

FIG. 14 is another embodiment showing a cap 1 having annular ridge 17 with a generally parallel epipedonal cross sectional area which mates and locks with an annular groove 18 having a corresponding parallel-epipedonal cross sectional area on body 2.

Figure 15:
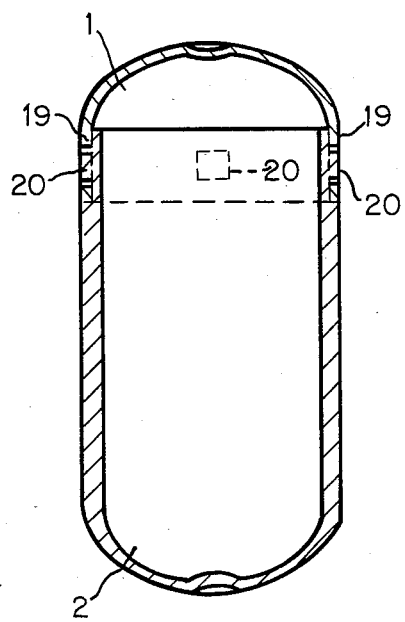
FIG. 15 is a cross-sectional view of a capsule provided with a locking window.

FIG. 15 is another embodiment of the invention, showing a cap 1 having one or more windows 20 arranged on its cylindrical side walls near the open end on a circular path which is coaxial with the axis of the capsule. The body 2 has a corresponding number of locking cams 19 which are protuberances located on its cylindrical side walls near its open end. These cams 19 mate with the windows 20 in locking engagement when the capsule parts are joined.

Figure 16:
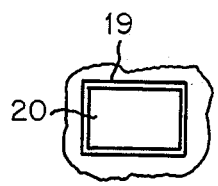
FIGS. 16 to 20 are partial cross-sectional views showing further embodiments of the locking window of FIG. 15.
Figure 17:
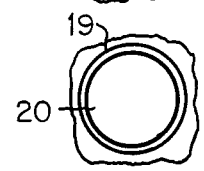
Figure 18:
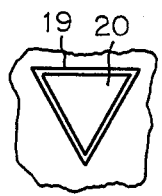
Figure 19:
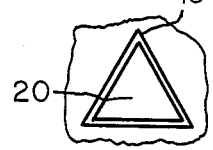
Figure 20:
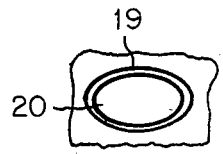

FIGS. 16 to 20 show alternate embodiments of the locking window 20 and cam 19 of FIG. 15: in FIG. 16, the cross sectional area is rectangular; in FIG. 17, circular; in FIGS. 18 and 19, triangular; and in FIG. 20, oval.

Figure 21:
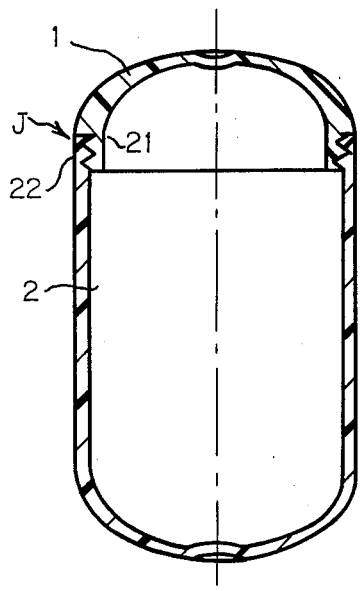

FIG. 21 shows an alternate embodiment of the present invention wherein the cap 1 has a male thread 21 on the outside surface of its cylindrical side walls at its open end. The male thread 21 engages with a female thread 22 on the inside surface of the body 2 at its open end. It is another feature of this embodiment that the body 2 and the cap 1 can be joined with an outside smooth surface, as at J, so as to make separation more difficult, thereby enhancing the locking feature of the capsule.

Figure 22:
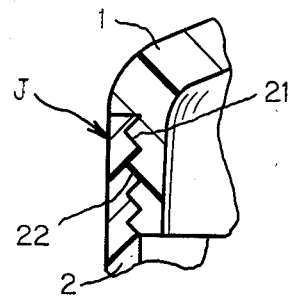
FIG. 22 is a partial cross-sectional enlargement of FIG. 21.

FIG. 22 is a partial enlargement of FIG. 21 showing the mating engagement of the male thread 21 with the female thread 22 in the vicinity of the smooth surface at the joining area, J.

Figure 23:
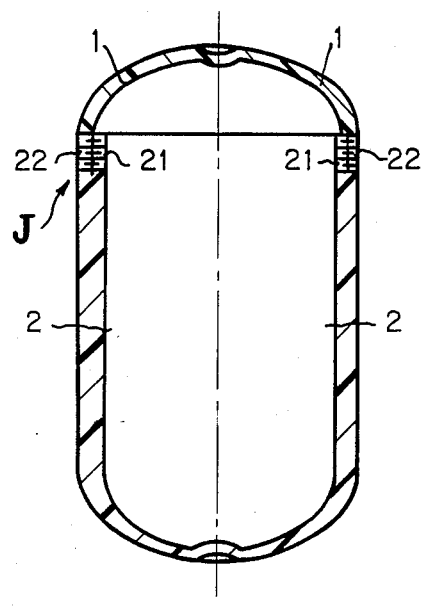
FIG. 23 is a cross-sectional view of another capsule.

FIG. 23 is an alternate embodiment of FIG. 21 wherein the body 2 has a male thread at the outside surface of its open end. The male thread 21 mates and engages with a female thread 22 on the inside surface at the open end of cap 1.

Figure 24:
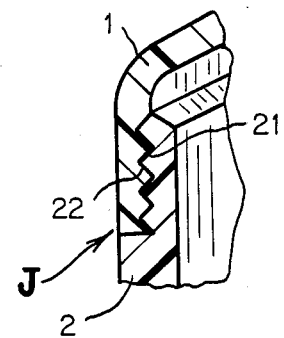
FIG. 24 is a partial cross-sectional enlargement of FIG. 23.

FIG. 24 is a partial enlargement of FIG. 23 showing the smooth surface at the joining area, J.

Figure 25:
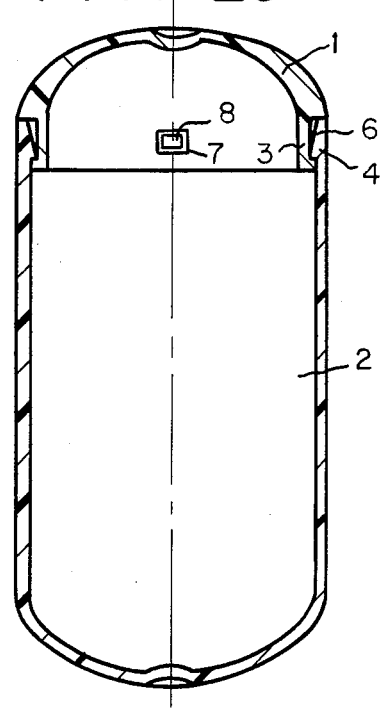
FIGS. 25 to 38 are cross-sectional views of various capsules according to the invention.

FIG. 25 shows a further embodiment of the invention having a bayonet-type locking arrangement wherein the cap 1 has an annular rectangular groove 3 adjacent to the open end of the cap 1 in a direction generally parallel to the capsule axis. The body 2 has a triangular ridge 4 on the inside surface at the open end of the body 2. The triangular ridge 4 has a conical taper 6 at its leading edge in order that the open end of body 2 can enter more easily within cap 1. In addition, cap 1 has a window 7 for mating with a protruding cam 8 on body 2. The combination of the groove 3 in engagement with ridge 4 plus the engagement of window 7 with cam 8 provides a secure bayonet-type lock.

Figure 26:
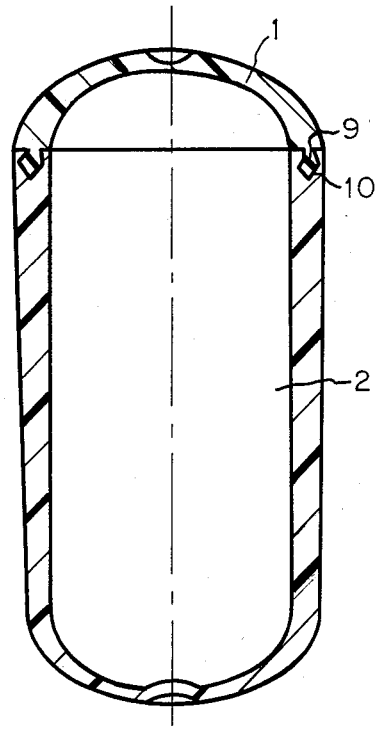

FIG. 26 depicts an alternate embodiment of the invention wherein the cap 1 has an annular dove-tail ring 9 on its cylindrical side wall at its open end for mating engagement with a dove-tailed groove 10 on the cylindrical side wall at the open end of the body 2.

Figure 27:
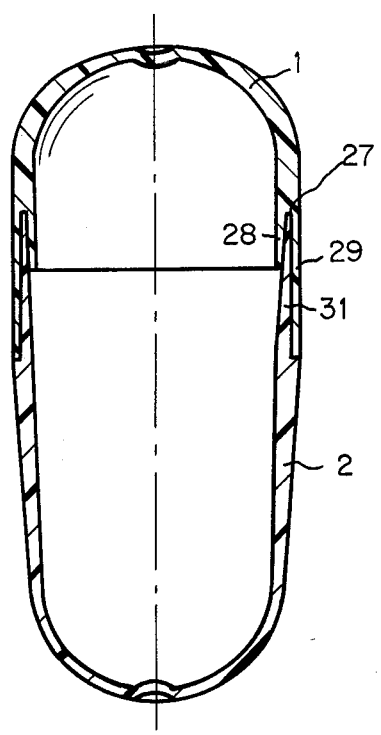

FIG. 27 shows an alternate embodiment of the invention wherein the cap 1 is provided, on its cylindrical side wall at its open end, with an annular slit 27 which is symmetrically arranged with respect to the main axis of the capsule. The slit 27 is defined by two annular wall parts 28, 29 of different lengths. The body 2 has an upright side wall 31 of reduced thickness which tapers towards its open end. In the joined position, as shown in FIG. 27, the side wall 31 of the body 2 is held by flexible pressure in the annular slit 27 which preferably has a correspondingly tapered configuration.

Figure 28:
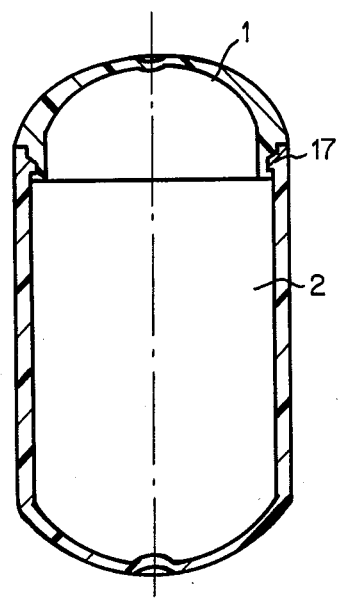
Figure 29:
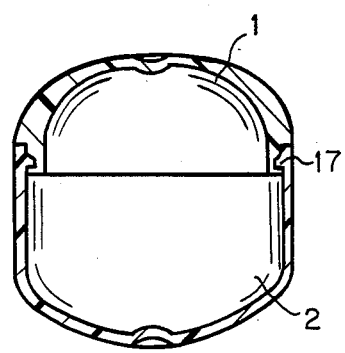
Figure 30:
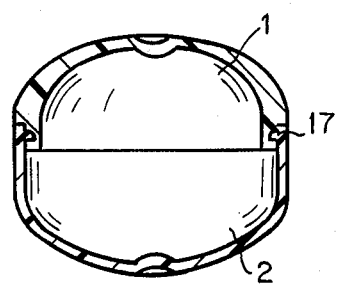

According to FIGS. 28, 29 and 30, a capsule is shown having a cap 1 joined with a body 2. At the joining area a locking means, as at 17, is provided in accordance with the embodiments previously disclosed. It is a feature of the present invention that the ratio can be variable between the outside diameter of the cylindrical side walls (D) and the overall length of the joined capsule (L). FIG. 28 shows a capsule wherein the ratio of D to L is less than 1. In FIG. 29, the capsule has a ratio of equal to 1, while in FIG. 30, the ratio is greater than 1. The advantages of a variable D to L ratio are that:

The volumetric contents of the capsule can be changed to meet particular requirements, especially for pharmaceutical and food use; and
the configuration can be varied to enable easier swallowing of the capsule, especially for pharmaceutical and food use, with children, adults and geriatric patients, who differ markedly in their ability to swallow capsules;

It is most advantageous, however, to utilize a capsule having a D to L ratio of equal to or greater than 1.

Figure 31:
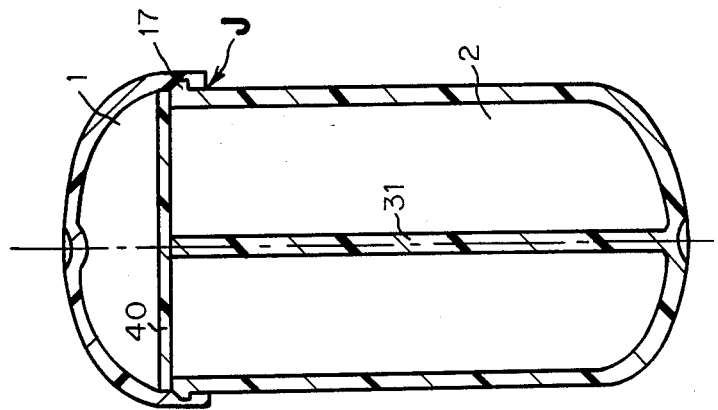
Figure 32:
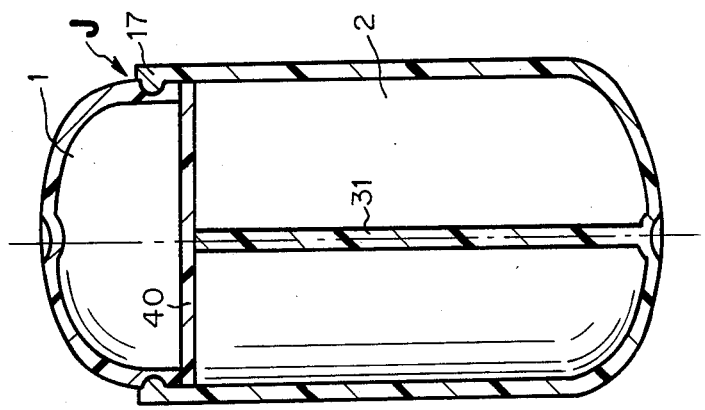
Figure 33:
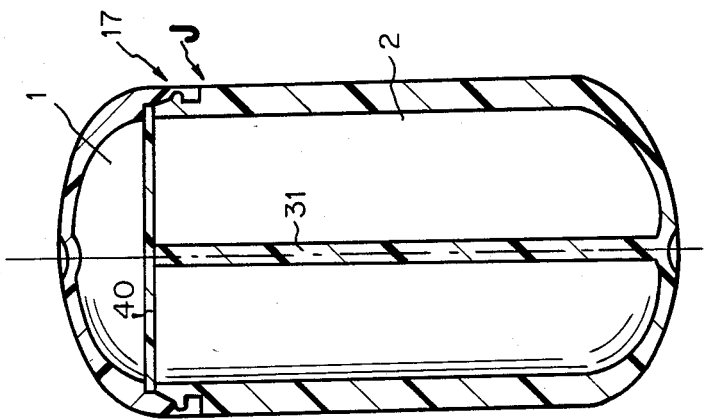

FIGS. 31, 32 and 33 show different embodiments of the invention having a cap 1 and a body 2 with a locking means, 17, in accordance with the embodiments previously disclosed. Each of these embodiments is constructed with a longitudinal partition 31 oriented parallel to the length of the capsule in order to divide body 2 into a plurality of compartments. If desired, each compartment may then be filled with a different medicament in various therapeutic dosages. Across the top of body 2 may be fitted a cover plate 40 in the form of a disc for preventing the interaction of entrapped air with the medicaments contained therein, certain of which may be deleteriously affected by contact with air.

FIG. 31 shows, as a feature of the present invention that the locking means 17 can be utilized with a .apsule having a smooth outside surface at the joinder, J. FIG. 32 shows a capsule as described above having a body 2 with a protruding edge at the joinder, J, while FIG. 33 shows a capsule as described above having a cap 1 with another protruding edge at J.

Figure 34:
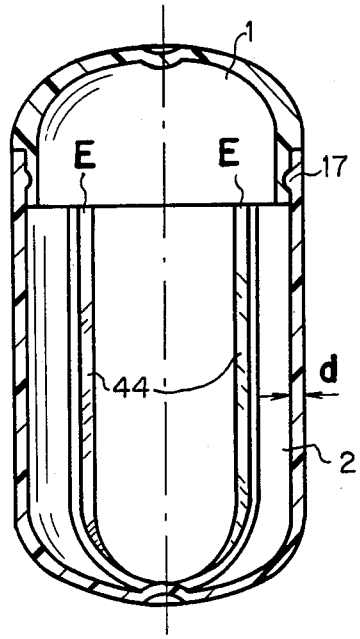

FIG. 34 shows a further embodiment of the present invention. The cap 1 and the body 2 have locking means at 17 as previously disclosed. In addition, the body 2 has on its side wall inner surface, a number of reinforcing ribs 44, which are molded so as to protrude from the inner side wall surface. The ribs 44 preferably extend over the whole length of the body 2 and join each other in the center of the closed end of the body 2. In the construction of the ribs 44, which may have triangular, rectangular or of other cross sections, the bending strength or rigidity of the body 2 is increased to such an extent that the wall thickness, D, may be substantially reduced. In addition, the end faces, E, of the ribs 44 form a stop and support means for the cap 1. The body 2 may be manufactured by injection molding, and the ribs 44 constitute a flow path for the injected materials so that the quick and regular distribution of the material is facilitated within the injection mold.

Alternatively, the ribs 44 in the above figure could be undercut into the side on one or both parts so as to improve the disintegration of the capsule in the gastrointestinal tract of the patient. Also, the ribs 44 could be molded with and protruded from the side wall outer surface of the body 2.

Figure 35:
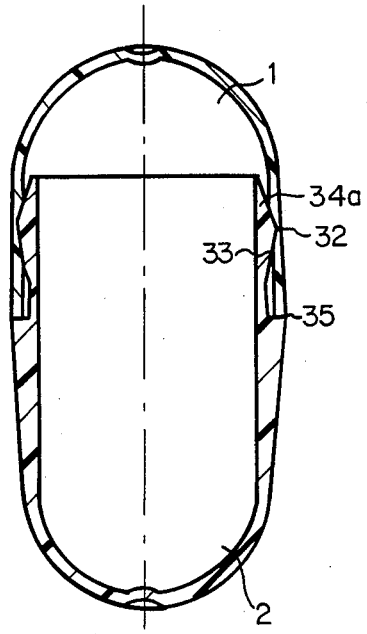

In the embodiment of FIG. 35, cap 1 has, on the inner surface of its cylindrical side wall, an annular groove 32 for receiving a conically shaped portion 33 of the cylindrical side wall of the body 2. The open end of the cap 1 rests upon the annular surface 35 of a shoulder formed in the side wall of the body 2. Joining of the cap 1 and body 2 is facilitated by tapered closed end 34 of body 2.

Figure 36:
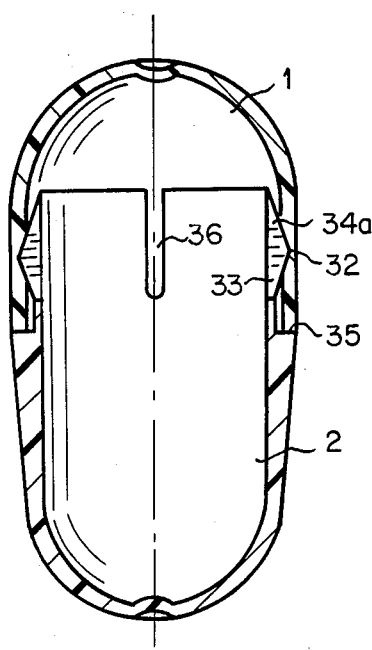

In FIG. 36 the reference numerals of FIG. 35 are used for all parts which have remained unchanged. The cap 1 is identical to that shown in FIG. 35. However, the body 2 is additionally provided with a slit 36 (one or more circumferentially arranged slits may be provided) which confers upon the open end of the body a greater flexibility, thereby assisting and simplifying the joining of cap and body.

Figure 37:
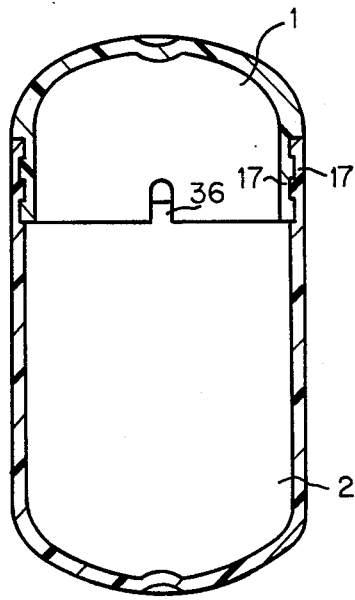

FIG. 37 shows an alternate embodiment of the present invention wherein the cap 1 and body 2 are provided with two or more locking means 17. In addition, the cap part is provided with slit means 36 for greater flexibility which assists and simplifies the joining operation of cap 1 and body 2.

Figure 38:
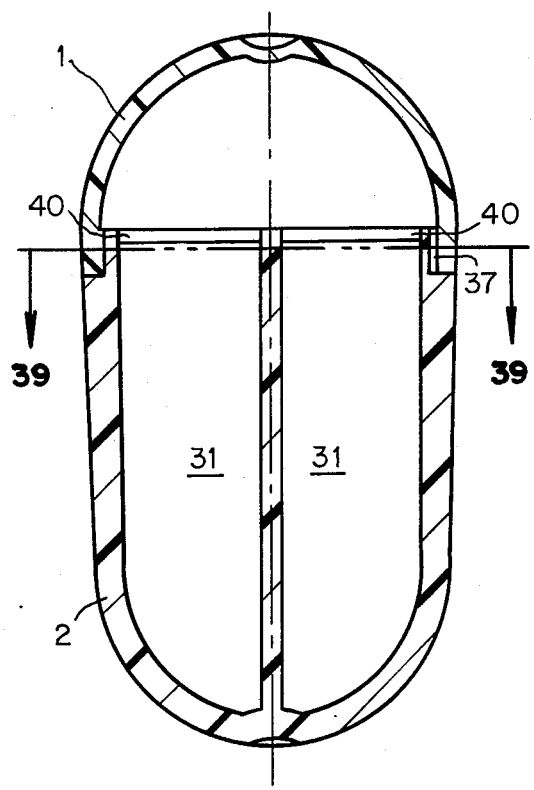

FIG. 38 shows an alternative embodiment of the capsule depicted in FIGS. 31–33 wherein body 2 is divided into at least four separate compartments by the presence of at least two longitudinal partitions 31, positioned perpendicularly to one another along the longitudinal axis of the capsule. These compartments may be filled with the same or complimentary medicaments 30 which are protected from mixing with one another and also of interacting with air entrapped within the capsule by the provision of a disc-like cover plate 40. In addition, in an alternate method for securing a locking engagement, cap 1 and body 2 are each provided with one or more ratchet teeth 37 on their surfaces facing each other, as shown in FIG. 39.

Figure 39:
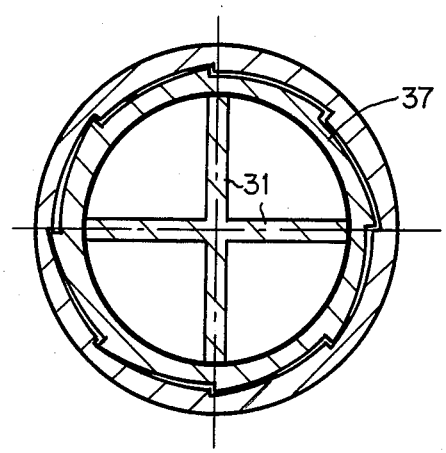
FIG. 39 is a cross-sectional view along line 39—39 of FIG. 38.

FIG. 39 is a sectional view of FIG. 38 showing the teeth 37 in mating engagement.

Figure 40:
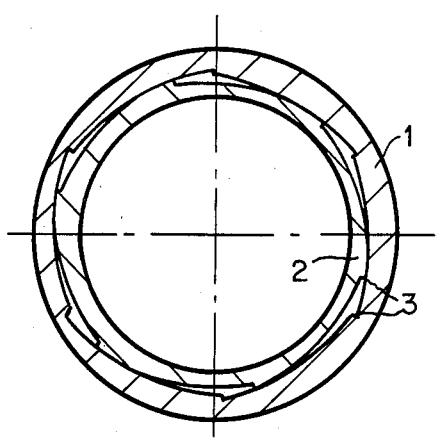
FIG. 40 is a view of FIG. 39 wherein one capsule part is axially rotated with respect to the other capsule part.

FIG. 40 is an alternate sectional view of FIG. 38 showing the position of teeth 37 when not in mating engagement with each other. The application of torque by coaxial rotation of one of the capsule parts around the other causes a frictional locking engagement of the teeth 37 of one capsule part upon the mating surface of the other capsule part.

Figure 41:
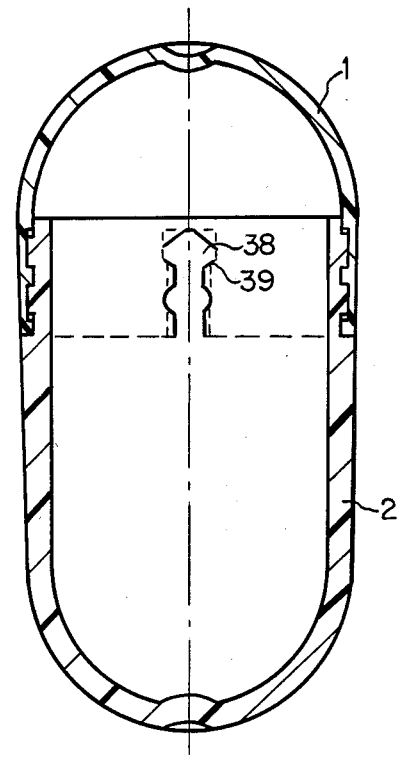
FIG. 41 is a side view of another capsule.

FIG. 41 is a side view of a further embodiment of the present invention wherein the body 2 is provided with one or more protrusions 38 on the outside surface of its side wall adjacent the open end which snaps into locking engagement with a corresponding recess 39 in the side wall of the cap 1.

Figure 42:
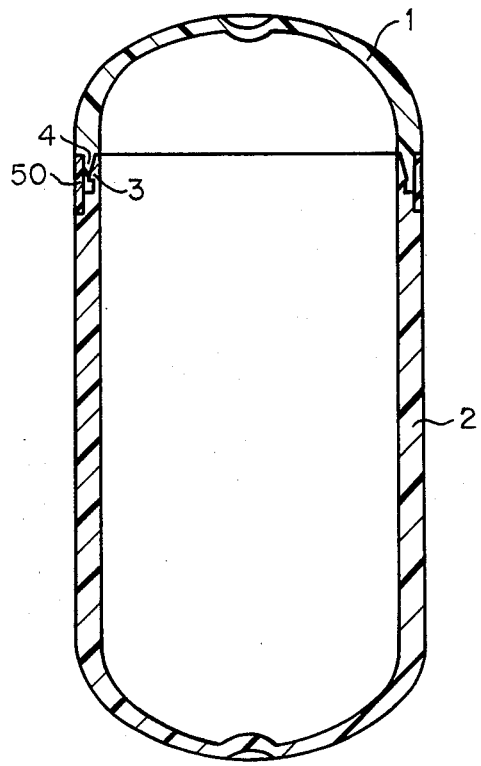
FIGS. 42 and 43 are cross-sectional views of additional capsules.

FIG. 42 is a still further embodiment of the present invention showing the cap 1 and the body 2 in locking engagement; both the cap 1 and the body 2 have a recessed groove 4 in the joining area which is filled by a band 50 of sealing or bonding material.

In any of the above embodiments, the body 2 may have a reduced diameter at the open end to facilitate entry during joining with cap 1.

FIGS. 4–31 and 34–44 show that the outside surface of the injection molded capsule is smooth in the joining area of the cap and body.

Capsules manufactured by the prior art dip-molding processes have the following disadvantages:
the air trapped in the spherical closed end of the cap of the filled and closed capsule results in a moving bubble of air when the content is a liquid;
numerous capsule contents, especially those which are creamy or liquid, may deteriorate after exposure to the oxygen in the trapped air;
such capsules are neither liquid- nor gas-tight;
the capsules are neither tamper-proof nor separation-resistant. There is a disadvantage if such a capsule, especially one containing food or drugs, can be opened or tampered with; and
when used for pharmaceutical purposes, the protruding edge located on the periphery of the open end of the capsule is relatively sharp. The removal of that protruding edge would make the capsule more attractive to swallow.

In comparison thereto, the present invention provides a capsule having a structural configuration which avoids the aforementioned disadvantages. The capsules of the present invention, in addition to being separation-resistant, avoid the entrapment of air during filling.

FIGS. 42, 42A, 43 and 43A show additional views of alternate locking devices. Any of the disclosed locking means may be used on any of the capsule shapes depicted in this specification.

The present invention also permits the preparation of distinctive capsule shapes by die-pressure molding of the above described materials.

Prior art pharmaceutical capsules have axially joinable cylindrical cap and body parts which require that the inner diameter of the cap side wall frictionally engages the outer diameter of the body side wall. When the cap and body are joined, the open end of the cap forms a relatively sharp protruding edge. The prior art capsules have the following principal disadvantages:
due to the limitations of manufacture by conventional dip-molding processes, the prior art capsules cannot differ much in their shapes and are, therefor, not very adaptable;
identification of the capsule contents must be indicated by means of different colors and imprinting, i.e. only by visual means and not by a combination of visual means and palpable characteristics; and
confusion of prior art capsules with different contents may occur because of the limited number of distinctive shapes available.

These principal disadvantages are becoming more serious because the number of oral medications is increasing and there are only a limited number of visual means for identification.

Prior art capsules also have the following further limitations:
they cannot be provided with a smooth outer surface which would render them easy-to-swallow; and
they have a relatively large empty space which causes a waste of material and of package volume.

It is therefore an object of the present invention to provide a capsule which has an adapted shape so as to avoid the aforementioned disadvantages and limitations. In view of the above, it is convenient to group several of the embodiments of the present invention into the following categories:

1. Capsules with a shape which is distinctive

The distinctively capsules of this group help to avoid confusion and to support a palpable identification of the capsule. For convenience, all of the figures in this application use the same reference numerals.

Figure 44:
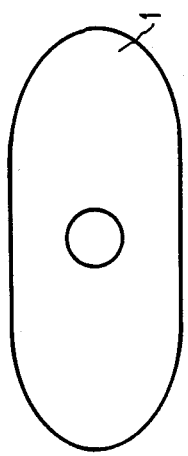
FIGS. 44, 46 and 48 are side views of capsules which have a distinctive shape.
Figure 45:
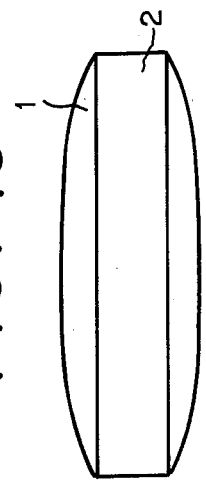
FIGS. 45, 47 and 49 are top plan views of the capsules of FIGS. 44, 46 and 48, respectively.
Figure 46:
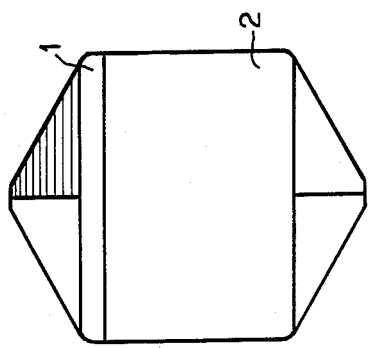
Figure 47:
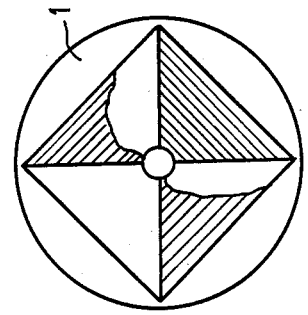

FIGS. 44 and 45 illustrate a distinctive oval-shaped capsule of the present invention having a cap 1 and a body 2. FIGS. 46 and 47 illustrate a pyramidical end-shaped capsule.

Figure 49:
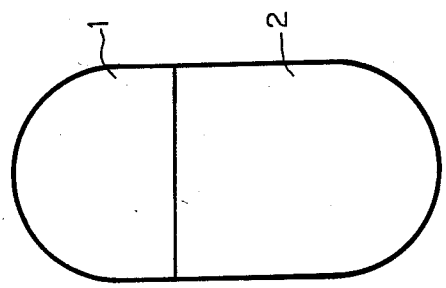
Figure 48:
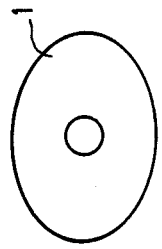
Figure 50:
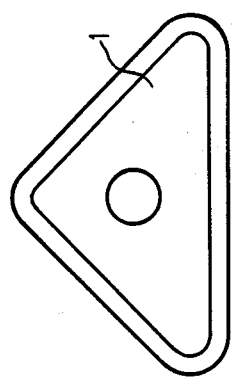
FIG. 50 is a top plan view of another capsule.
Figure 52:
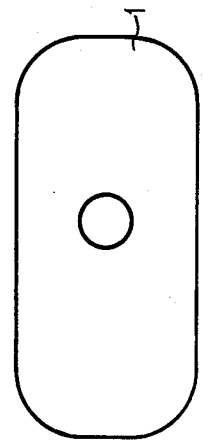
FIGS. 52, 54 and 56 are top plan views of additional capsules, each of which have a distinctive shape.
Figure 51:
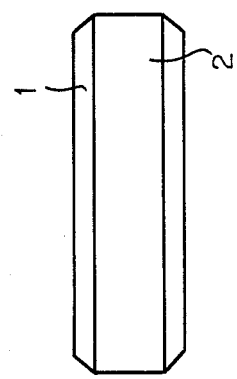
FIG. 51 is a cross-sectional side view of the capsule of FIG. 50.
Figure 53:
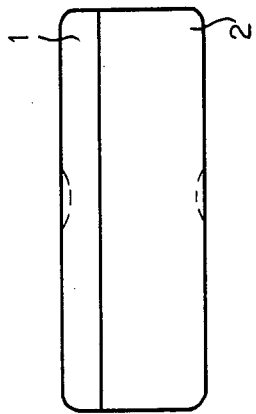
FIGS. 53, 55 and 57 are side views of the capsules of FIGS. 52, 54 and 56, respectively.

FIG. 48 is a side view of an alternate embodiment showing a flat capsule. FIG. 49 is a top plan view of FIG. 48 showing the elongated oval-shaped capsule. FIG. 50 is a refinement of the embodiment of FIGS. 48 and 49 showing a modified oval-shaped capsule. FIG. 51 is a sectional side view of FIG. 50 showing the side walls of cap 2 completely overlapping the side walls of body 1 when joined. Also shown is the smooth outer surface of side walls at the joining area, J. The use of completely overlapping side walls and a smooth outer surface at the joining area make it difficult for potential tamperers to grip and separate the capsule parts. FIGS. 52 and 53 are of another refinement of the embodiments of FIGS. 48, 49, 50 and 51 showing a rectangular oval-shaped capsule.

Figure 54:
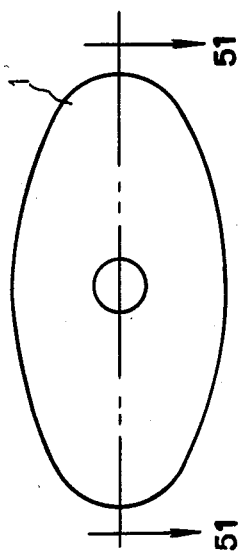
Figure 55:
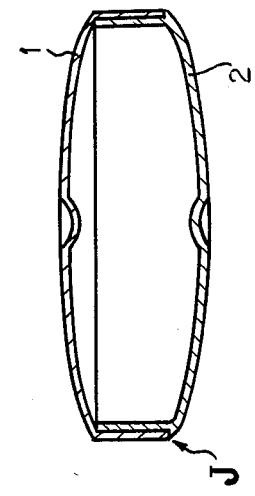
Figure 56:
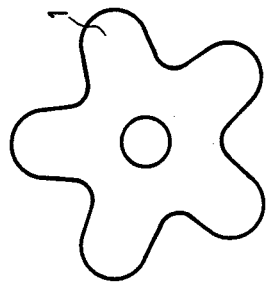
Figure 57:
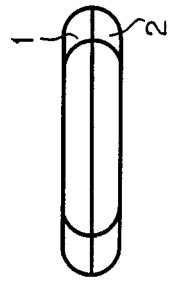

FIGS. 54 and 55 are views of a triangular-shaped capsule while FIGS. 56 and 57 illustrate a star-shaped capsule.

2. Capsules having a shape which corresponds to a vendor's logogram

The logo-shaped capsules of this group help to identify the vendor. The logo of imaginary companies has been utilized in FIGS. 58-61.

Figure 61:
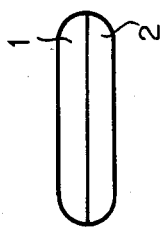
FIGS. 59 and 61 are side views of the capsules of FIGS. 58 and 60, respectively.
Figure 60:
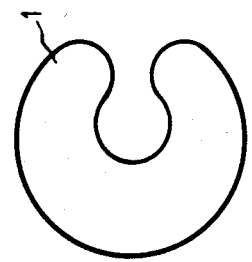
FIGS. 58 and 60 are top plan views of capsules manufactured in a shape corresponding to a vendor's logo.
Figure 59:
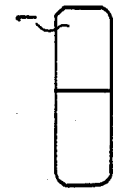
Figure 58:
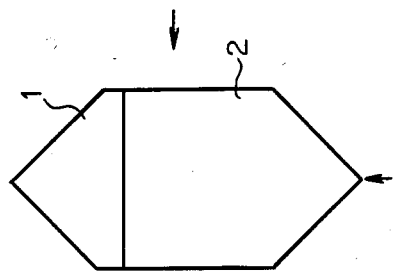

FIGS. 58 and 59 are views of a parallelolipodonal-shaped capsule logogram. FIGS. 60 and 61 are views of a C-shaped capsule logogram. With the use of the new injection-molding processes to produce capsules, a great variety of shapes, including all the letters of the alphabet, in various forms, is now obtainable. This is in marked contrast to the severe limitations of prior art hard shell capsule shapes made with dip-molding methods.

3. Capsules with a shape which indicates their purpose

Figure 62:
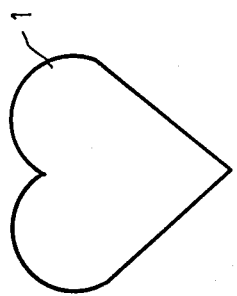
FIG. 62 is a top plan view of a capsule which is shaped to indicate its purpose.
Figure 63:
FIG. 63 is a side view of the capsule of FIG. 62.

The purpose-shaped capsules of this group help to indicate their field of application. As shown in FIGS. 62 and 63, the heart shape indicates the field of coronary care.

4. Capsules with a shape indicating their dosage form

Figure 64:
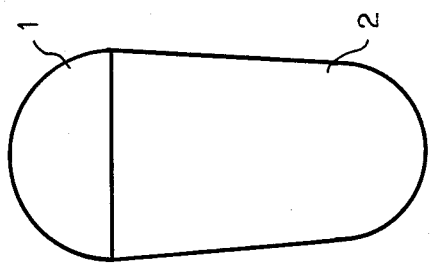
FIG. 64 is a side view of a capsule having a shape representing its dosage form.
Figure 65:
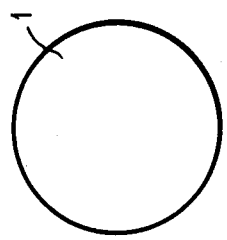
FIG. 65 is a top plan view of the capsule of FIG. 64.

The dosage-shape capsules of this group indicate their use for other than the oral route of administration. FIGS. 64 and 65 show a suppository-shaped capsule suitable for rectal application. It should be further understood by those skilled in the art that the above embodiments may enable the production of two-piece hard shell capsules with palpable shapes that can be recognized by visually impaired patients.

5. Capsules with a shape which provides a varying volume of contents

Figure 66:
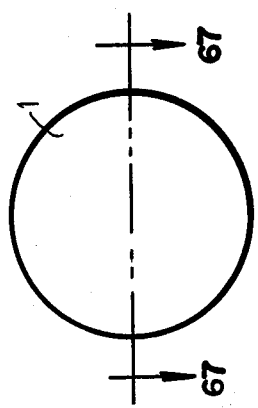
FIGS. 66 and 68 are side views of capsules which provide for a varying volume of contents.
Figure 67:
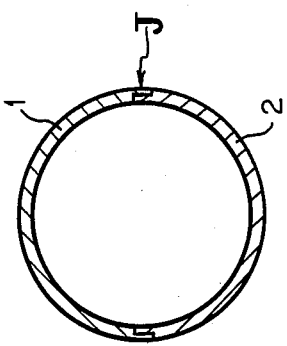
FIGS. 67 and 69 are cross-sectional views taken along line 67—67 of FIG. 66, and 69—69 of FIG. 68, respectively.
Figure 68:
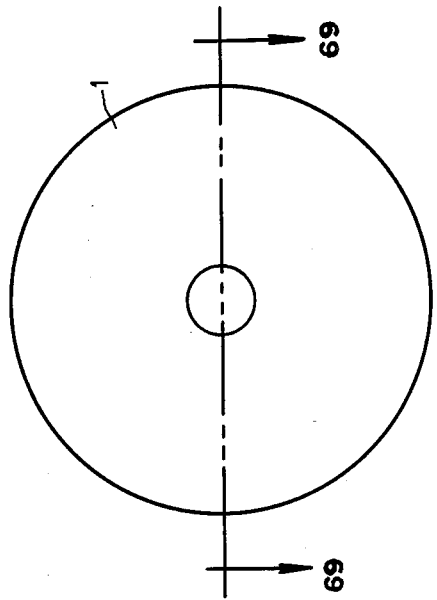
Figure 69:
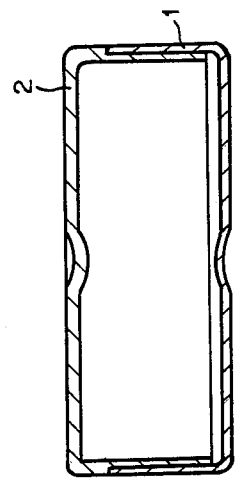

The embodiments of this group provide varying volumes of contents for the same size capsule. FIGS. 66 and 67 show a spherical shape providing the smallest possible package for the largest volume of contents. These figures also show separation-resistant locking means at the side walls of cap 1 and body 2 at the joining area J. FIGS. 68 and 69 show a disc-shaped configuration which provides one of the largest possible packages for the smallest volume of contents. The great variety of capsule shapes produced by the injection molding process provides great flexibility in the manufacture of hard shell capsules with varying package to volume ratios.

Figure 71:
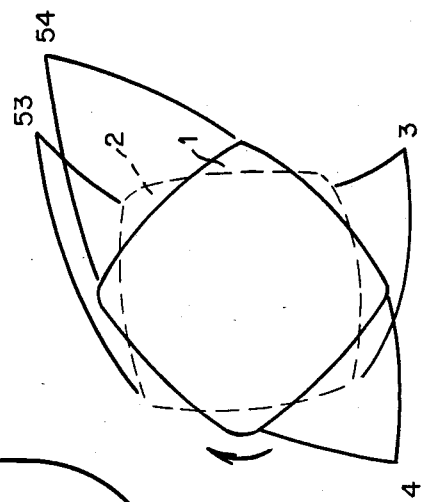
FIG. 71 is a top plan view of the capsule of FIG. 70.
Figure 70:
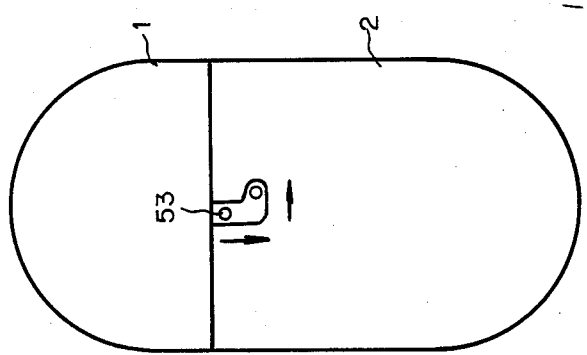
FIG. 70 is a side view of a capsule having a shape which enables precise positioning on a joining machine.

6. Capsules with a shape which enables a precise positioning on a joining machine There are various capsules which need an exact positioning of the two capsule parts before joining, e.g., a threaded or bayonet-type lock engagement. This precise positioning can be achieved by means of a locator on the outer surface of the capsule. FIGS. 70 and 71 are views of such an embodiment, showing four locating positions possible with respect to the rotary angle around the capsule axis. This is a significant advantage over a conventional dipmolded capsule which has a circular cross-sectional area. In FIG. 70, a capsule with four possible positions is shown having a bayonet-type locking arrangement illustrated as, e.g., four protruding cams 53 on one part which mate with four corresponding ridges 54 on the other part. In FIG. 71, another bayonet-type closure system is shown as having an axial and a rotational movement of the body 2 with cap 1. (Axial and rotational movement is shown by dotted lines.)

It will be understood by those skilled in the art that there are capsule shapes of the present invention which meet the characteristics of more than one of the above mentioned groups.

In a further embodiment of the invention, the injection molded capsules are manufactured so as to provide bossed imprinting of letters or designs thereon.

Prior art capsules are imprinted using an ink composition. This process is very complicated and requires an additional step. Furthermore, it is difficult to imprint the closed ends of the capsule. With the bossed imprinting of the present invention, it is possible to obtain an imprinted capsule without the use of chemical inks. Thus, the imprinted capsule may be fully natural.

The capsule of the present invention may also be achieved by injection molding the capsule parts with a mold which is provided with the desired imprinting (debossed or embossed) of letters or designs therein. The manufacturing and imprinting of the capsules may therefor be achieved in a single step. Furthermore, during debossing by injection molding, the capsule material is not adversely affected as in the prior art when the imprinting is made by a hot stamp. When a hot stamp is used, there is also the disadvantage that a second processing step is necessary. Also, when using a hot stamp, embossing is not possible.

FIGS. 72 and 73 are views of an embodiment of the present invention showing a joined capsule having cap 1 and body 2. Imprinted on the outside surface of the side wall of the cap is the embossing 55 of the letters in the name of the vendor CAPSUGEL. Such imprinting is not possible with the prior art dip-molding process, but such embossing can be achieved with the new injection molding process. The present invention may also include a method for sealing or bonding of the joined capsule parts which provides additional securing of the capsule. This connection further impedes separation and tampering. Such sealing or bonding also makes the capsule liquid, moisture, vapor and gastight.

For starch and many of the starch derivatives it has been surprisingly found that wetting the joining surfaces of the cap and the body parts with water at room temperature without additional heating produces an excellent effect, the capsule being absolutely liquid and tamper-proof.

It is also known that tablets provide a way for patients to choose the dosage by breaking the tablet into pieces. With the present invention, it is possible to utilize injection molding techniques to make combinations of two or more medicaments which cannot be combined in a tablet or in a prior art capsule because they tend to react with each other to yield toxic or otherwise unsuitable products. With the present invention capsule dosage forms can be provided which can be divided into subunits to be swallowed.

The dosage form of this invention may also consist of two or more capsules which are connected to each other. The connections between the capsules may be manufactured simultaneously with the capsule by die-molding techniques and may consist of the same material as the capsules themselves. The capsules may be divided by breaking the connections.

The capsules may be formed with two or more non-separate compartments within each capsule for containing different medicaments therein. Further, both the divisible and the compartmented capsules may be formed simultaneously as a multiple unit dosage or package.

Prior art hard shell capsules for pharmaceutical use consist of one unit which has only one filling compartment formed by axially joinable cylindrical cap and body parts. Due to manufacturing limitations imposed by the prior art dip-molding process, the prior art capsules cannot be attached one to another during the manufacturing process.

In addition, with the present invention, it is possible to provide capsules to be filled with two or more different medicaments.

The present invention relates to die pressure molded and shaped articles formed by the die pressure molding of starch, or starch derivatives, all with a low water content.

The present invention especially relates to certain structures and forms of such die-molded capsules, especially injection-molded capsules.

The present invention concerns die-molded articles, particularly injection-molded capsules having a body part and a cap part, each having a side wall, an open end and a closed end, the two parts being joinable, characterized in that such capsules are made:

(i) from a starch or a starch composition having a water content of 5-25% by weight (calculated to the starch composition);
(ii) by high speed die-molding; and
(iii) that the cap part is die-molded as a stopper directly onto the open end of the body part after the body has been filled so a to seal the contents within the capsule; or
(iv) that each of said cap and body parts has in the side wall area, adjacent to its open end, at least one locking means, said locking means being arranged to face each other to achieve, after joining of said parts, a separation-resistant connection; the capsule having a plurality of compartments and the cap and body parts being worked at a precision of 0.01% and the capsule being stable in dimensions.

A special feature of such capsule according to (iv) is that at least one part of the open end has the side wall portion recessed with an annular shoulder for receiving and for constituting a stop means in the joining area for the side wall portion at its open end of the other part, both side wall portions being shaped so that the outside surface is smooth in the joining area of said two parts.

A further feature of such capsules according to (iv) is that the inner surface of the cap, when said cap is mounted on the open end of said body, is at practically the same level or below the level of the horizontal plane touching the open end of the cylindrical side wall of said body, whereby, after the filing of the contents and after the closing of said cap and body, practically no air is trapped between said inner surface of said cap and the surface of said contents.

Capsules prepared by the present invention have the further advantage that they can be die-molded so as to be joined in a distinctive shape to provide a palpable identification of the capsule.

t is also possible to prepare capsules according to the present invention where as mentioned above, the cap and/or the body have embossed printing of letters thereon.

A further embodiment of this invention is the complete liquid proof sealing of the cap and body parts by wetting the joining surfaces with water.

Articles prepared by the present invention have the further advantage that they can be die-molded so as to be joined in a distinctive shape to provide a palpable identification of the capsule.

Such capsules can, according to this invention, be made from starch by the method of die-molding. They can be useful for the exact dosage of solid, creamy and liquid substances, especially for pharmaceutical use, said capsule having two parts, a cap part and a body part which are joinable; each of said capsule parts having a side wall, an open end and a closed end.

In the detailed description it is convenient to group several of the embodiments of the present invention into three categories:

1. Divisible Capsules

Figure 76:
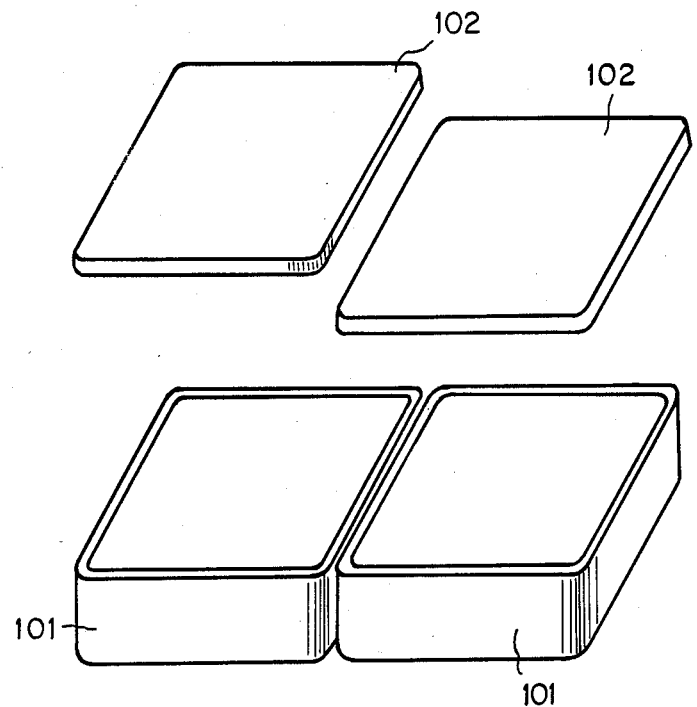
FIG. 76 is an exploded view of the capsule of FIG. 74.
Figure 77:
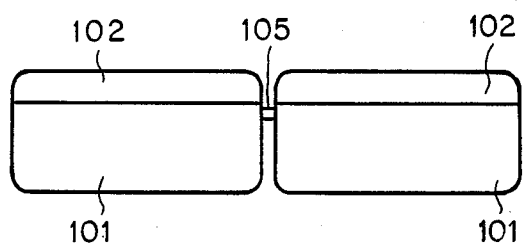
FIG. 77 is a side view of the capsule of FIG. 76.
Figure 80:
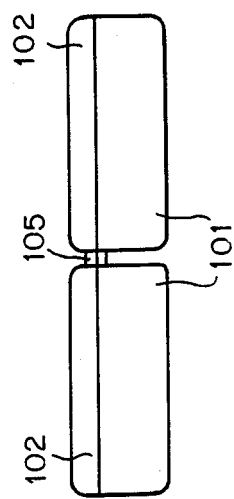
FIGS. 80-85 depict alternate embodiments of a divisible capsule wherein the body and cap parts are joined by a connecting lamella.
Figure 81:
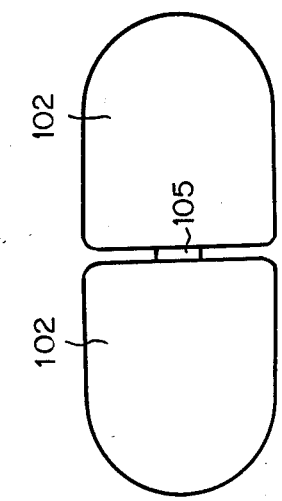

The divisible capsule form can be swallowed as a whole, or it can be separated into pieces which can be swallowed individually. Embodiments of this group are shown in FIGS. 74, 75, 76, and 77. FIG. 74 is a perspective view of a divisible capsule consisting of two subunits 109, 110 comprising two bodies 101 and two caps 102. As shown in FIG. 75, the two bodies 101 are connected by a weak joining lamella 105. The two caps 102 are not connected. In FIG. 76 the dosage form is shown after filling but before the caps 102 are put onto the bodies 101. FIG. 77 is a side view of FIG. 76 after the caps 102 have been put onto the bodies 101. The embodiment shown in the FIGS. 74 to 77 may be swallowed as a whole capsule in the initial state but this dosage form can also be swallowed individually after it has been separated into two subunits along the lamella 105.

The two subunits of the divisible capsule shown in FIGS. 74 to 77 may be filled with different or with the same medicaments. In cases where both subunits are filled with the same medicament, the amount of the dosage can be divided by breaking the form into two pieces. In cases where the capsule is filled with two different medicaments--one in each subunit--the desired medicament can be swallowed by breaking the capsule at the lamella. In order to identify the content of each subunit, the colors of the subunit may be different or the subunits may be differently imprinted.

The capsule parts 101, 102 and the connecting lamella 105 can be manufactured simultaneously by die-molding and preferably by injection-molding. The lamella 105 consists of the same material as the capsule parts 101 and 102.

Figure 78:
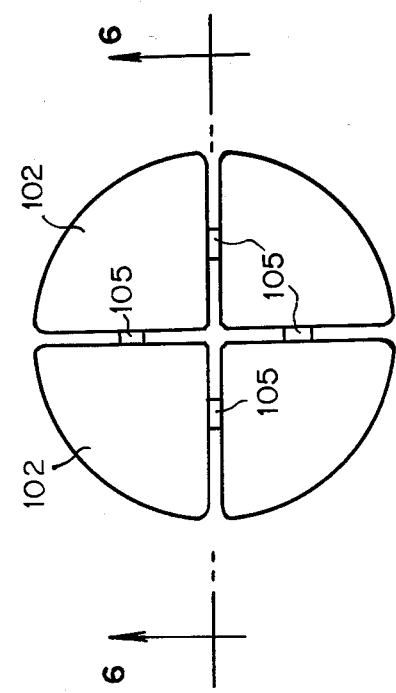
FIG. 78 is a top plan view of a divisible capsule consisting of four subunits.
Figure 79:
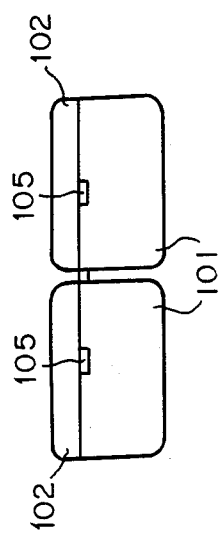
FIG. 79 is a side view of the capsule of FIG. 78.

FIGS. 78 and 79 show another embodiment of a capsule having four subunits. FIGS. 78 and 79 show four caps 102 and four bodies 101 connected by weak lamellas 105 so as to provide breaking possibilities. This embodiment may be swallowed as a whole or as three, two or only one subunit. Also, the different subunits of the capsule may be filled with different or the same medicaments.

Figure 84:
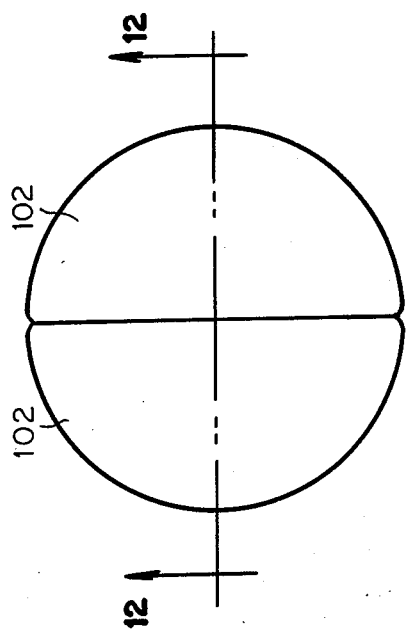
Figure 85:
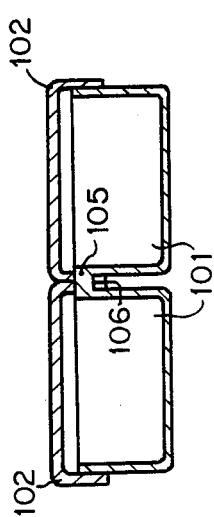
Figure 82:
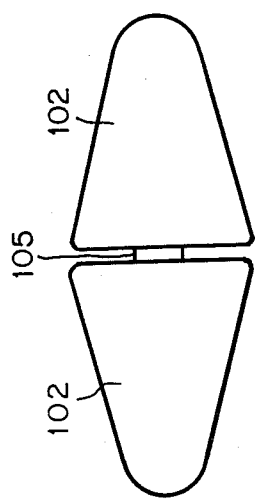
Figure 83:
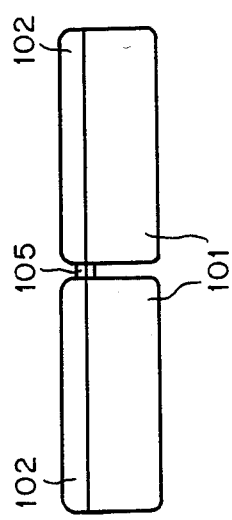

Alternate embodiments are shown in FIGS. 80 to 85, using the same reference numerals as those used in FIGS. 74 to 79. In these embodiments the bodies 101 and caps 102 are connected by weak lamellas 105. As shown in FIGS. 84 and 85, the caps 102 may overlap the bodies 101. Also, the caps 102 may have a recess 106 at the place where the connecting lamella 105 is located, so that the lamella 105 is not seen from the top of the capsule and is hardly visible after the capsule has been broken into its subunits.

Figure 86:
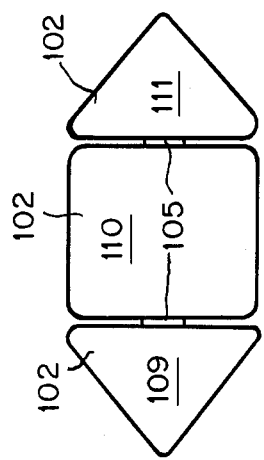
FIGS. 86-89 depict further alternate embodiments of a divisible capsule wherein only the body parts are joined by connecting lamella.
Figure 87:
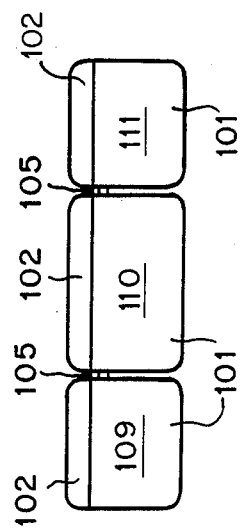
Figure 88:
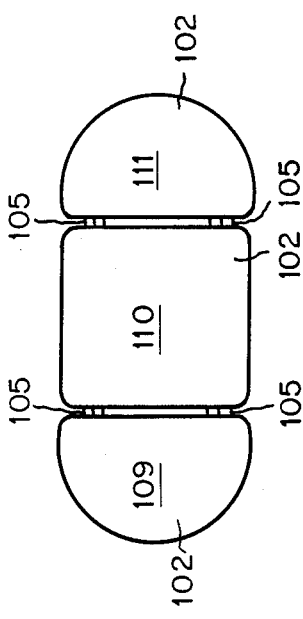
Figure 89:
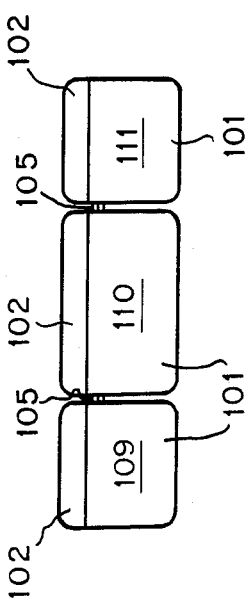

Another embodiment is shown in FIGS. 86 and 87, wherein the capsule has three subunits 109, 110, 111 having an inner and two outer parts, each of which again consists of a body 101 and cap 102. In FIGS. 86 and 87, the outer parts are formed as triangles. Alternately, the outer parts in the FIGS. 88 and 89 have the shape of semicircles. In embodiments of the FIGS. 86 to 89, only the bodies 101 are connected by the lamellas 105, whereas the caps 102 are separate pieces.

2. Compartmented Capsule

The compartmented capsule has two or more compartments for medicaments. It cannot be broken into subunits but it can be filled with two or more different medicaments to be swallowed simultaneously. It is an advantage of the die-molding technique that the number of the compartments is not limited to two but can be varied as required by the application.

Figure 90:
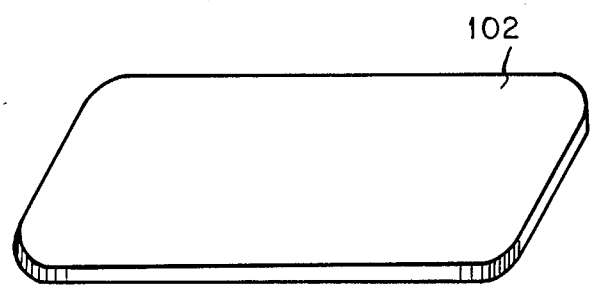
FIG. 90 is an exploded perspective view of a compartmented capsule.
Figure 90:
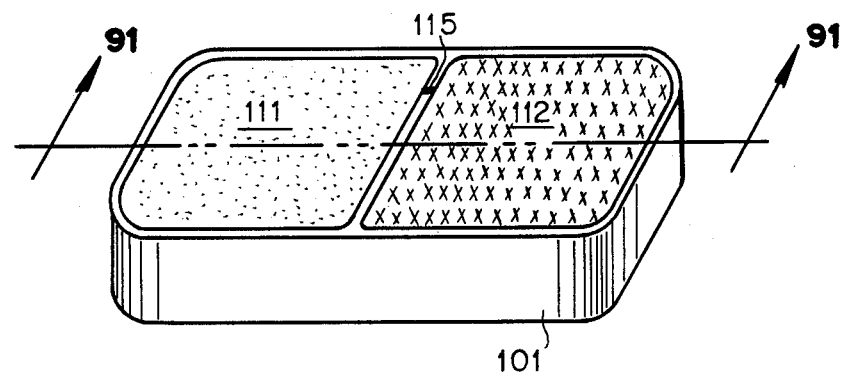
Figure 91:
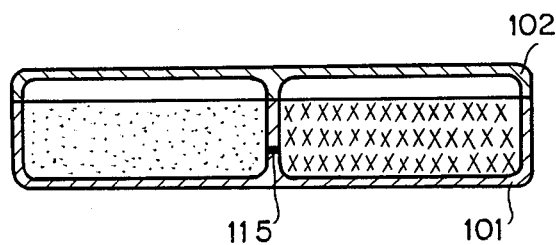
FIG. 91 is a cross-sectional view of the capsule of FIG. 90 taken along line 91—91.

An embodiment of this group is shown in FIGS. 90 and 91. FIG. 90 is an exploded perspective view of a compartmented capsule having a cap 102 and a body 10I with two compartments 11, 112 therein separated by a partition 115. Each of the compartments 111, 112 contain different medicaments. FIG. 91 shows the complete separation of the different medicaments in compartments 111 and 112 when the capsule is closed.

Figure 92:
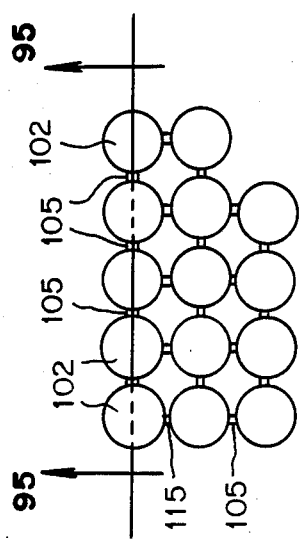
FIG. 92 is a top plan view of another compartmented capsule.
Figure 93:
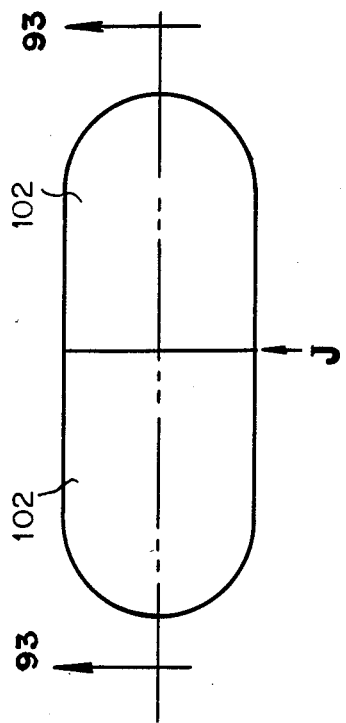
FIG. 93 is a sectional view of the capsule of FIG. 92 taken along line 93—93.

FIGS. 92 and 93 are views of a compartmented capsule of the present invention showing two caps 102 axially abutting together at their open ends. FIG. 93 also shows the two caps 102 abutting together at their open ends, but included within the caps 102 is a cylindrical body 116 which is divided by an integrally molded disc or partition 115 into two compartments 111, 112 for containing different medicaments. After filling the different medicaments into the compartments 111, 112, each of the two caps 102 are telescopically joined over the body 111 from each open end so as to confine the different medicaments therein. For different therapeutic requirements, one of the caps 111 could be made of a material soluble in the acid secretions of the stomach. The other cap 101 and the body 102 could be made of enteric materials. In this way, one of the medicaments in a compartment could be disintegrated within the stomach of the patient while a different medicament in the other compartment could be disintegrated in the intestinal tract of the patient. By varying the materials and/or the thicknesses of the caps 101 and the body 102, the disintegration rates of each compartment 111, 112 may be controlled.

It is another feature of this invention that the cap 101 and body 102 can be joined so as to provide a smooth surface at the joining area, J, as shown in FIGS. 91, 92 and 93.

3. Capsule Package

A capsule package consists of two or more capsules which are connected so that each subunit can be broken off as needed for use. Capsule packages are not intended to be swallowed as a whole but rather to provide a convenient storage form, e.g. when each subunit has to be taken periodically. Therefore, the number of connected subunits is not limited because of an easy-to-swallow requirement. The capsule packages may also be used to package the divisible capsule of group 1 and the compartmented capsule of group 2.

Figure 94:
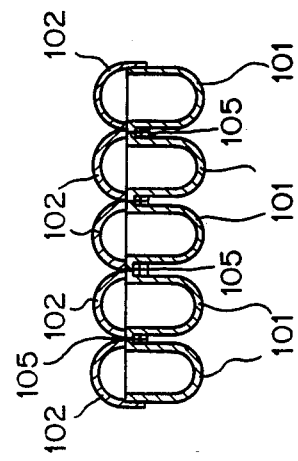
FIG. 94 is a top plan view of a capsule package showing the capsules aligned along their axes.
Figure 95:
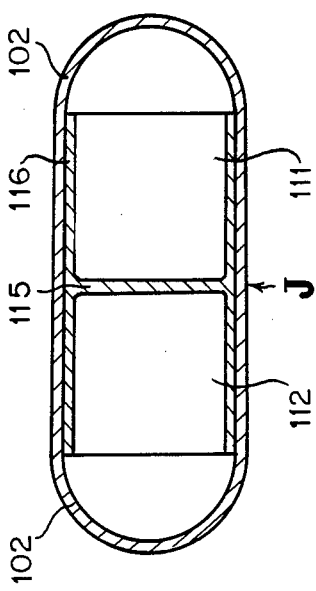
FIG. 95 is a sectional view of the capsule package of FIG. 94 taken along line 95—95.

An embodiment of this group is shown in FIGS. 94 and 95, which show the capsule bodies 101 connected by the lamellas 105 made of the same material as the capsule bodies 101 and which are manufactured simultaneously. The caps 102 of the dosage package are not connected to each other. Both the bodies 101 and the caps 102 may be provided with locking means so as to yield a separation-resistant arrangement.

Figure 96:
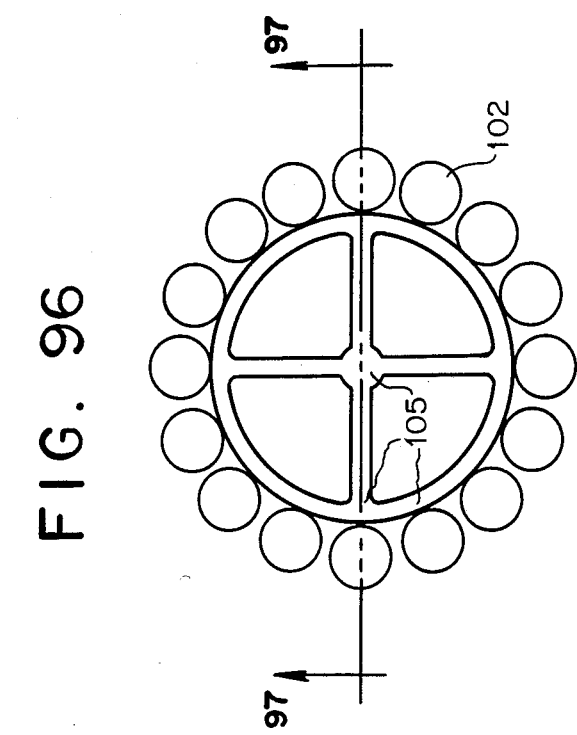
FIG. 96 depicts a top plan view of another capsule package configuration.
Figure 97:
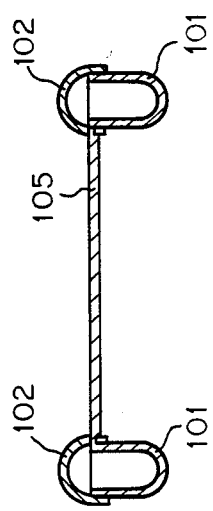
FIG. 97 is a sectional view of the capsule package of FIG. 96 taken along line 97—97.

Another embodiment of the capsule package is shown in FIGS. 96 and 97, which show the capsule bodies 101 connected by the lamella 105 which may be of the same material as the capsule bodies 101. These lamella 105 are manufactured simultaneously with the bodies 101. Also, both the bodies 101 and the caps 102 may be provided with any of the previously described locking means.

Figure 98:
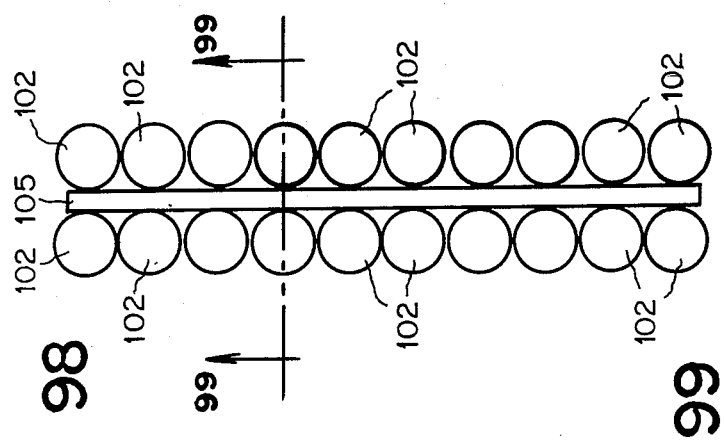
FIG. 98 depicts a top plan view of an alternate capsule package configuration.
Figure 99:
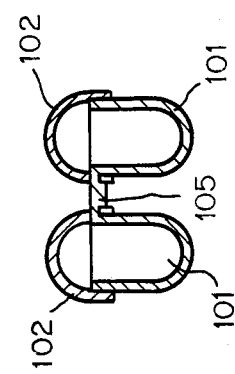
FIG. 99 is a sectional view of the capsule package of FIG. 98 taken along line 99—99.

An embodiment of the capsule package for the combination of two different medicaments is shown in FIGS. 98 and 99 which show a plurality of capsule bodies 101 and caps 102 which are formed simultaneously by die-molding. The bodies 101 are connected, while the caps 102 are not. The capsules are shown as arranged in two rows so that the two medicaments can be filled in adjoining bodies.

Blister packages are a known form of packaging for pharmaceutical dosages and other high-security products. It is another feature of the present invention that hard shell capsules can be formed from the blister package components of a blister sheet and a cover sheet which are sealed together by heat and pressure. Subsequently, the blisters are filled with medicaments. In this invention, the blister package components are manufactured from water soluble and edible starch compositions.

Figure 100:
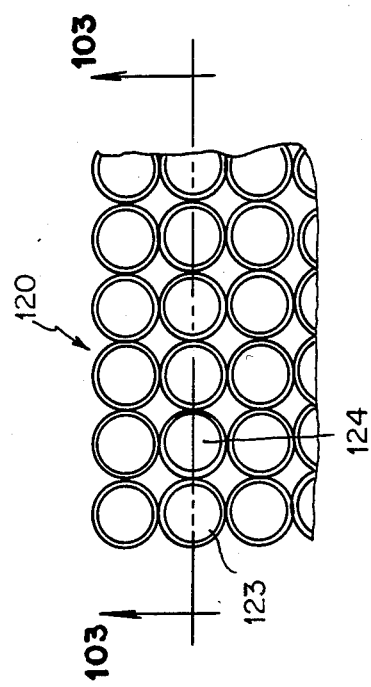
FIGS. 100 and 102 are top plan views of capsule blister packages.
Figure 101:
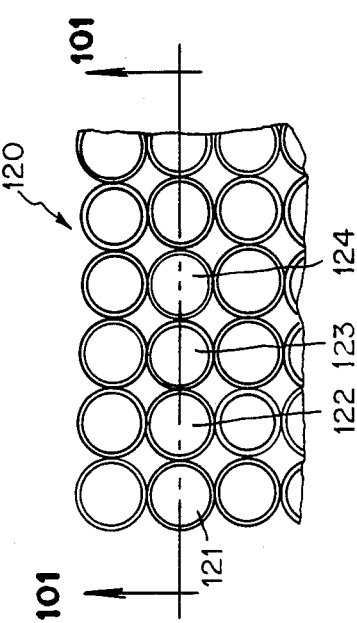
FIGS. 101 and 103 are cross-sectional views of the blister packages of FIGS. 100 and 102, taken along line 101—101 and 103—103, respectively.

FIGS. 100 and 101 are views of an embodiment of a capsule blister package, showing the blister sheet 120 having separate blister compartments 121, 122, 123, 124 . . . therein.

A cover sheet 125 is sealed by pressure and heated to the blister sheet 110 so as to seal the blister compartments 121, 122, 123, 124 . . . containing medicaments. At the juncture of the blister sheet 120 and cover sheet 125, there may be perforations 126 so as to close the separations of the blister compartments 123, 124 . . . FIGS. 102, 103, 104 and 105 show alternative embodiments of capsule blister packages using the same reference numerals as FIGS. 99 and 100.

Figure 102:
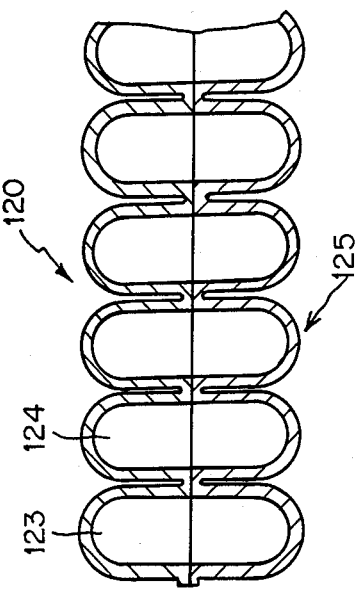
Figure 103:
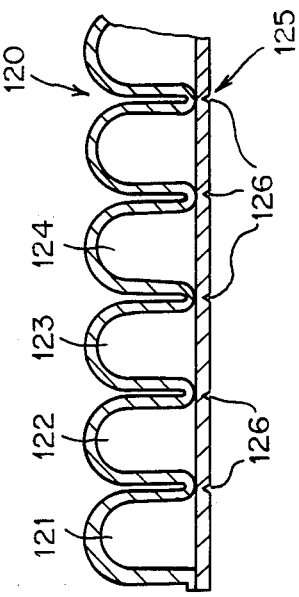

In FIGS. 102 and 103, the capsule blister package is shown having an elongated cross section of a conventional capsule form wherein the blister sheet 120 and cover sheet 125 have symmetrical compartments 123, 124 therein.

Figure 104:
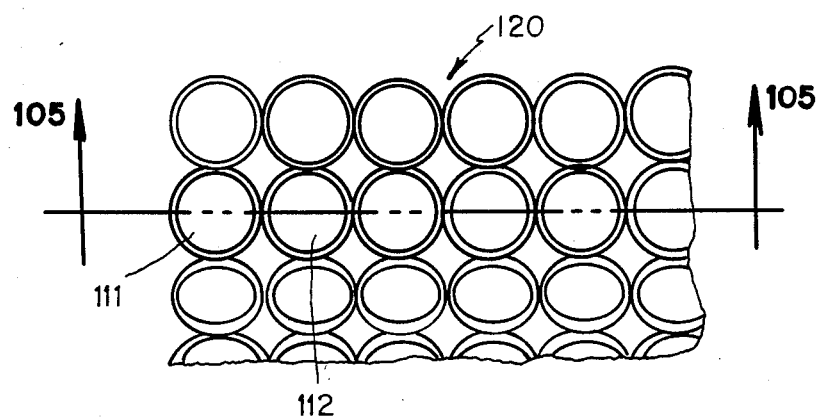
FIG. 104 is a top plan view of another blister package.
Figure 105:
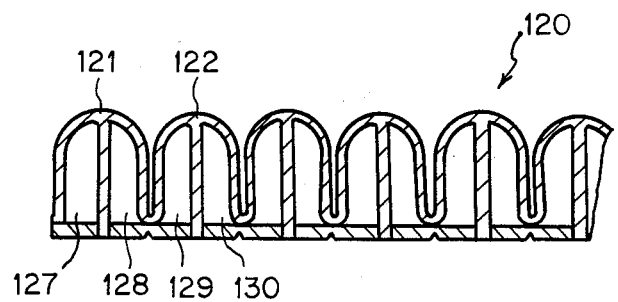
FIG. 105 is a sectional view of the embodiment of FIG. 104 taken along line 105—105.
Figure 108:
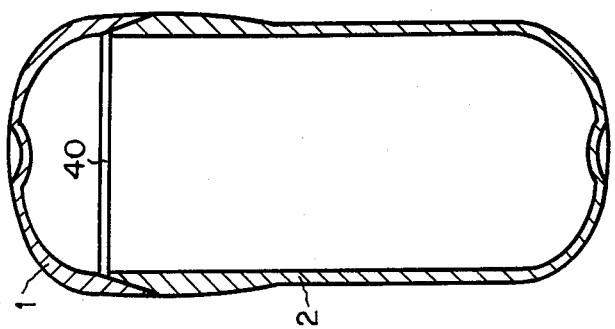
Figure 107:
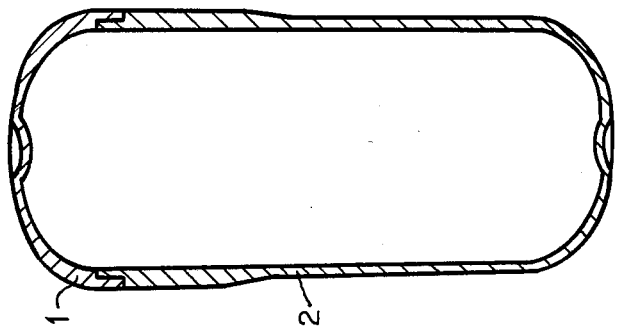
Figure 106:
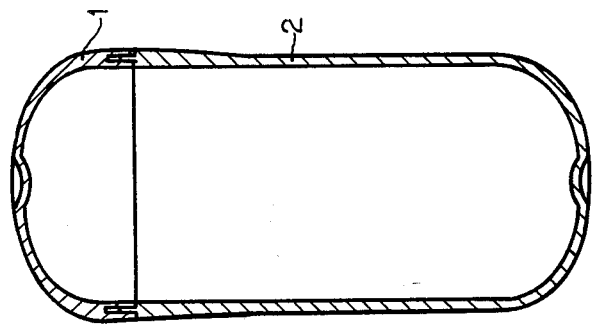

In FIGS. 104 and 105, the capsule blister package is shown with each compartment 121, 122 subdivided into subunits 127, 128, 129, 130, respectively, for containing different medicaments therein.

FIGS. 106–109 are sectional views of an embodiment of a pharmaceutical capsule similar to that depicted in FIG. 1C. While all four embodiments illustrated therein possess alternate arrangements for locking the cap 1 and body 2 of each capsule together in a tamper resistant configuration, FIG. 108 additionally illustrates the provision of a cover plate 40 placed across the upper portion of the body 2 to prevent the interaction of the medicaments stored therein with air entrapped beneath the inner surface of the cap 1, and, optionally, to provide an additional compartment.

FIG. 110 illustrates a capsule embodiment similar in many respects to the capsule depicted in FIG. 1D. This embodiment is provided with a window for receiving the locking tabs of the other capsule part. It is possible to provide a plurality of such windows on one capsule part with the same number of locking tabs on the other part.

FIGS. 111 and 112 illustrate a ridge and groove locking arrangement utilized to maintain the cap portion and the body portion in locking engagement. This embodiment is also provided with a cover plate 40 for insertion above the medicament 30 located in the body portion of the capsule.

FIG. 113 is a sectional view of an embodiment similar in many respects to the capsule depicted in FIG. 1A. This embodiment utilizes an alternate embodiment of the ridge and groove locking arrangement wherein a cover plate 40 placed perpendicular to the opening of the body 2 of the capsule to prevent the interaction of entrapped air with the medicament 30 located below.

Figure 114:
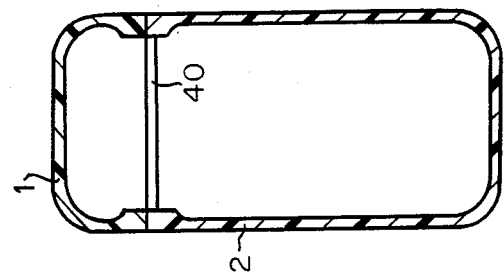
FIG. 114 is a top plan view of a capsule embodiment having two locking windows located in the cap portion.
Figure 115:
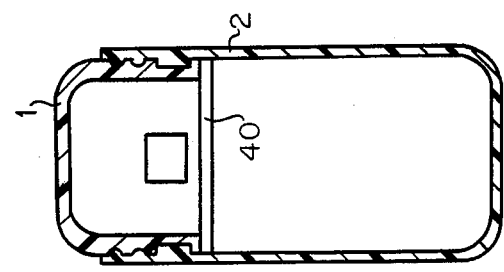
FIG. 115 is a cross-sectional view of the capsule of FIG. 114 taken along line 115—115.

FIGS. 114 and 115 depict an alternate embodiment of the capsule of FIG. 110 having two windows instead of one, and wherein the body 2 of the capsule has a smaller diameter than the cap 1. This dual ridge and groove locking assembly includes cover plate 40.

Figure 116A:
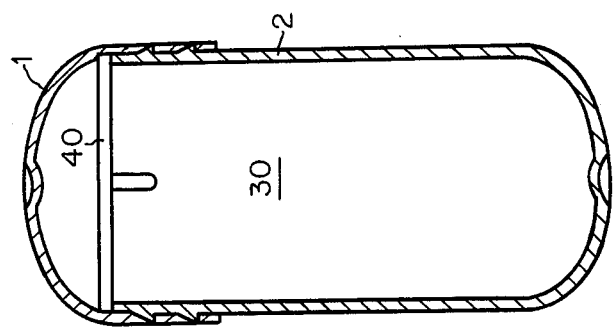
FIGS. 116(A) and (B) are cross-sectional views of alternate locking arrangements for various capsules.
Figure 116B:
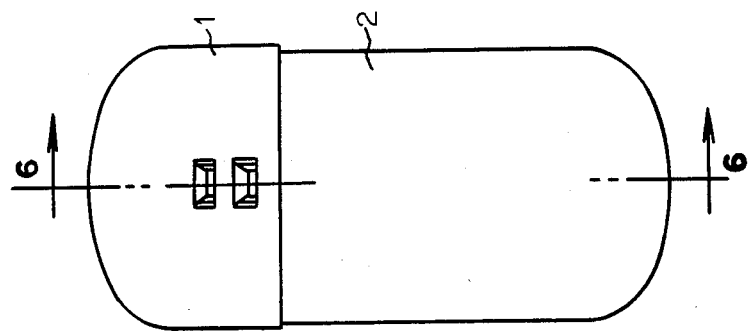

FIGS. 116A and B are sectional views of a capsule embodiment similar to that depicted in FIG. 1B. FIG. 116A has one locking window in the cap portion, the purpose of said window having been described earlier. Further, in FIG. 116A, there is an edge portion present on the outer surface of the capsule where the cap and body portions are joined. The embodiment depicted in FIG. 116B, shows a smooth outer surface in the same area. In addition, both embodiments are provided with a cover plate 40 for protecting the medicaments enclosed therein from the effects of entrapped air.

Figure 117:
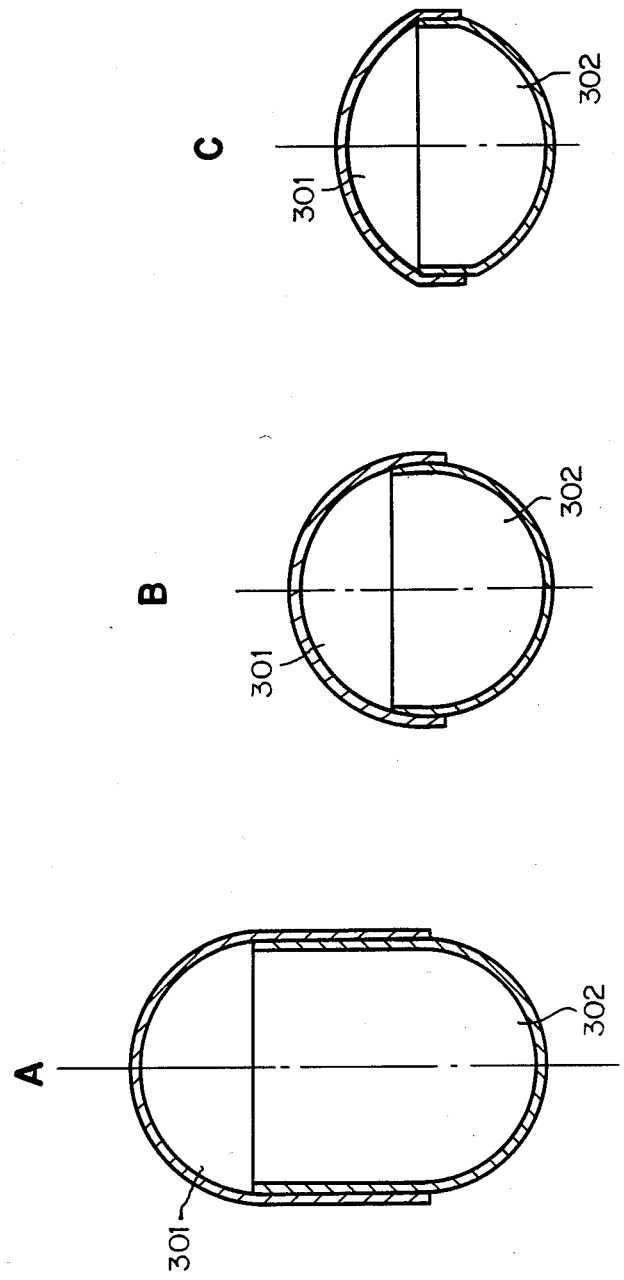
FIGS. 117(A), (B) and (C) are cross-sectional views of capsules configured so that their diameters are less than their length.

In FIGS. 117A, B and C, there are shown embodiments of capsules of the present invention similar to those depicted in FIGS. 28–30, but having no locking windows. These capsules have a cap 301 and a body 302 which may be filled with a pharmaceutical product to be swallowed by a patient. FIG. 117B and C show the preferred embodiments of the invention wherein the ratio of D equal to L is equal to or greater than 1, while FIG. 117A shows the typical capsule having a ratio of less than 1.

It is understood by those skilled in the capsule arts that there is an advantage with a variable D to L ratio in that the volumetric contents of the same diameter capsule can be changed to meet particular pharmaceutical dosage requirements. In addition, the most preferred capsule configuration has a D to L ratio of 1 or more so as to make the capsule more nearly in the squat configuration of a tablet. Also, the squat shape is psychologically easier to swallow by children, adults and geriatric patients who differ markedly in their ability to swallow capsules.

The present invention may also include sealing or bonding of the capsule and the capsule parts where joined. Sealing or bonding of the capsule parts provides an additional security which further impedes separation and tampering. This also takes the capsule, liquid, moisture vapor and gas-tight. The capsules produced in conformity with the present invention may be used for pharmaceutical purposes, as well as to provide an exact quantitative dosage of dyestuffs, chemicals, spices, fertilizing combinations for plants, fertilizers with protective substances, seeds, cosmetics, agricultural products, etc. The capsules of the present invention may also be used for the exact quantitative dosage of vitamins, foods, etc.

All of the embodiments of the present invention can be produced on injection-molding machines wherein the capsule material is melted in a plasticizing unit and then injected into a mold. When the mold is opened, the dosage parts are ejected. As dosage form materials one may use: starch, or other polymer materials including mixtures and foams of such materials, which are water-soluble, edible and suitable for casting or molding. Film casting, injection molding, compression molding, flow molding, deep drawing methods and other die-molding techniques may also be used for the production of the capsules of the present invention.

In addition to capsules, many useful products can be prepared by the injection molding of starch with the necessity of high form stability and minimum dimensional deviations. These products include candies, packaging containers for food-stuffs, pharmaceuticals, chemicals, dyestuffs, spices, fertilizing combinations, seeds, cosmetics and agricultural products and matrices of various shapes and size of starch compositions containing substances and/or active ingredients including food stuffs, pharmaceuticals, chemicals, dyestuffs, spices, fertilizing combinations, seeds, cosmetics and agricultural products, which are microdispersed within the matrix and released from it through disintegration and/or dissolution and/or bioerrosion and/or diffusion depending on the solubility characteristics of the used starch composition. Some of these products may also result in a controlled release delivery system for the enclosed substance.

Furthermore, medical and surgical products can be prepared by injection molding starch compositions. The biodegradable nature of starch makes it environmentally desirable over certain materials presently being used. In addition, the non-toxic nature of the materials further enhances their desirability as a material to be used in the injection molding industry.

Figure 118:
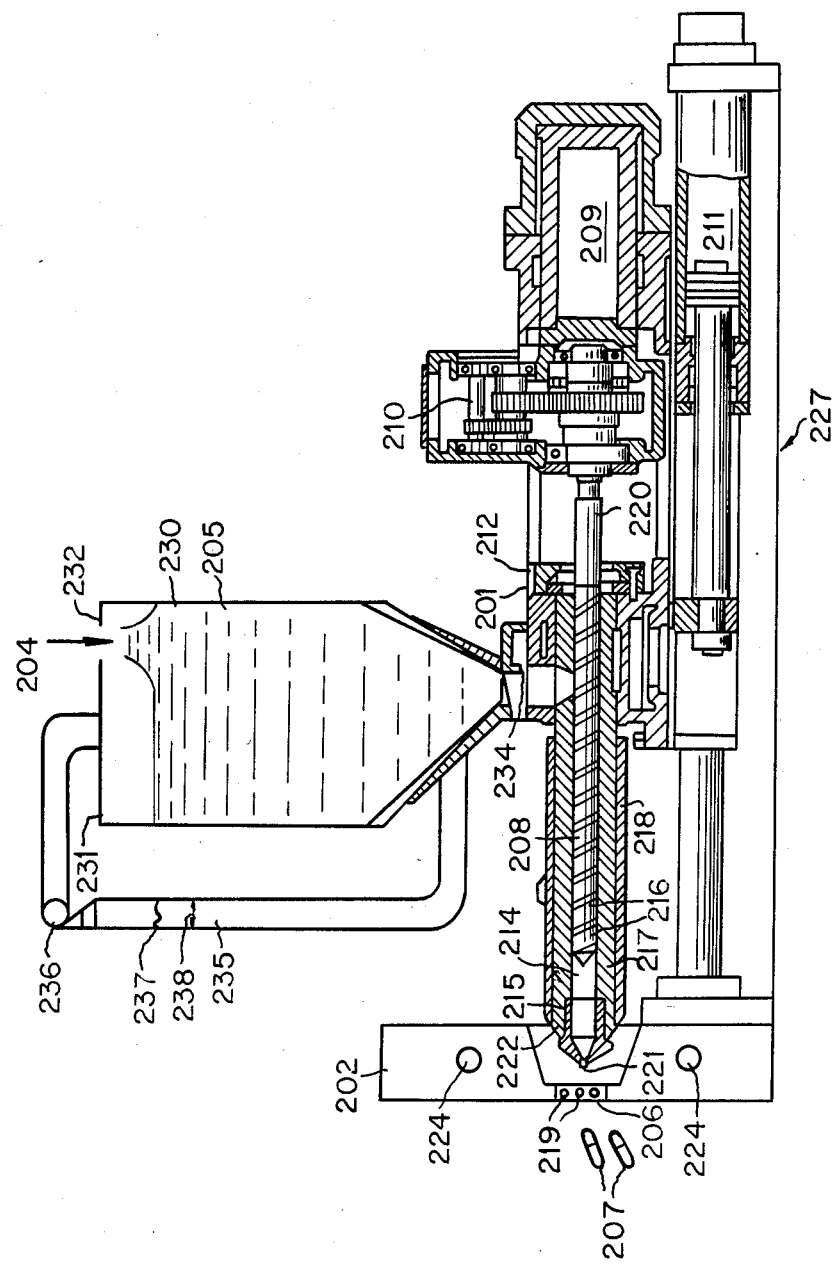
FIG. 118 is a schematic of a reciprocating screw injection molding device for making capsule parts.
Figure 118:
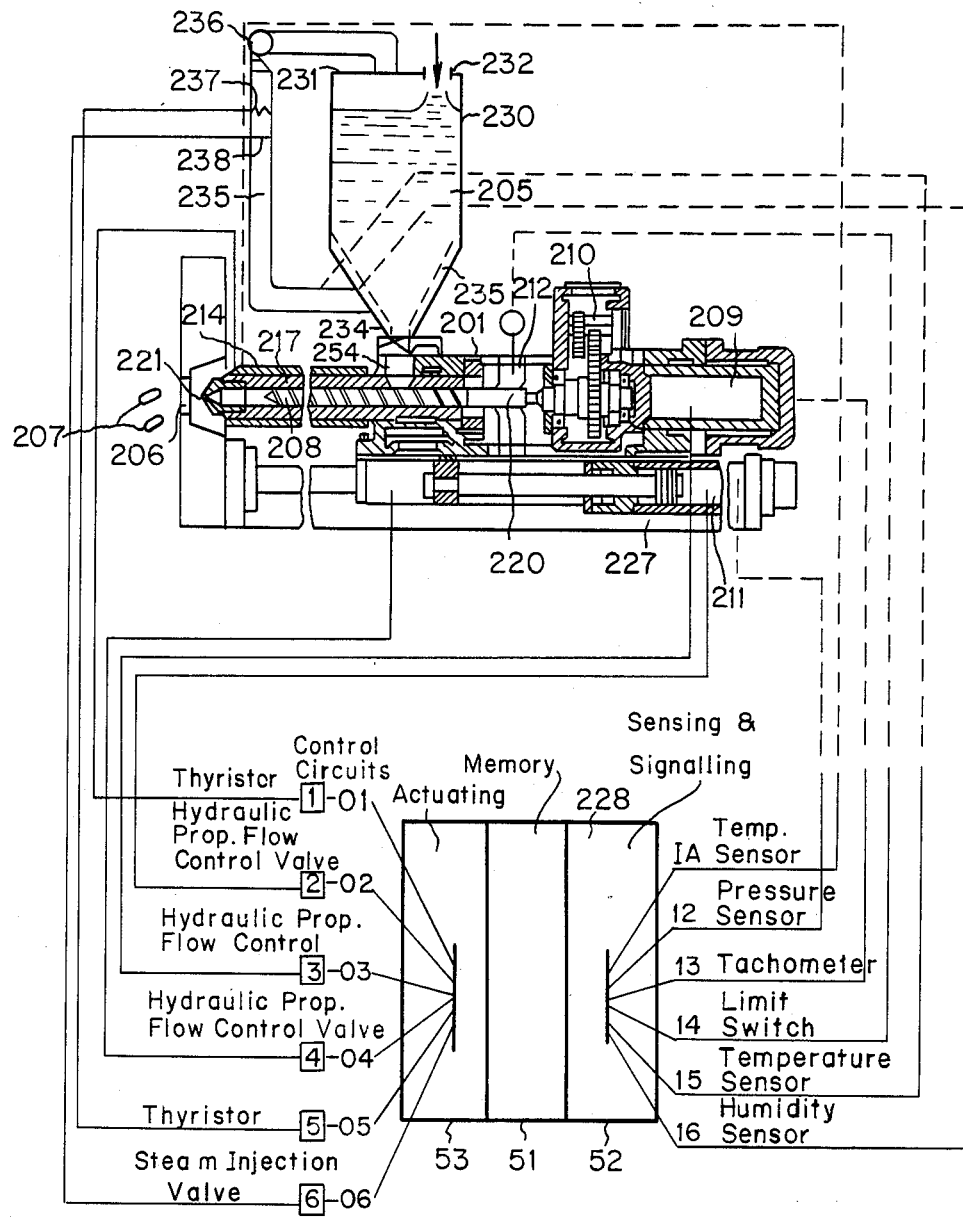

Referring now to FIG. 118, the injection molding device 227 for manufacturing capsules of the type described above generally consists of three units: a hopper unit 205, an injection unit 201 and a molding unit 202.

The function of the hopper unit 205 is receiving, storing, maintaining and feeding starch 204 at a constant temperature and at a constant water content. The hopper unit 205 comprises a vertical cylinder 230 having a closed top 231 with an inlet 232 therein to receive starch 204. At the bottom of the vertical cylinder 230 is a closed conical funnel 233 and a discharge outlet 234 to feed starch 204 into an inlet 234 of the injection unit 201. There is an air duct 235 communicating between the closed top 231 and the conical funnel 233 wherein air is circulated by a blower 236, the air temperature is maintained by a thyristor 237 and the relative humidity of the air is maintained by a steam injector 238.

The function of the injection unit 201 is melting, dissolving in water, and plasticizing in the extruder barrel 217 the starch 204 fed from the hopper unit 205 into the extruder inlet 254 and injecting the plasticized starch 214 into the molding unit 202.

The function of the molding unit 202 is automatically holding, opening and closing the mold 206 having capsule shaped cavities 219 therein, and ejecting the capsule parts 207 therefrom.

Within the injection unit 201 the screw 208 both rotates and undergoes axial reciprocal motion. When the screw 208 rotates, it performs the functions of melting, dissolving in water, and plasticizing the starch 204. When the screw 208 moves axially, it performs the functions of injecting by transporting and ramming the plasticized starch 214 into the mold 206. The screw 208 is rotated by a variable-speed hydraulic motor 209 and drive 210, and its axial motion is reciprocated by a duplex hydraulic cylinder 211.

Compression of the plasticized starch 214 in front of the rotating screw 208 forces back the screw assembly 220 containing the screw 208, the drive 210 and the motor 209. When the screw assembly 220 reaches a preset back position a limit switch 212 is contacted. When a defined time has elapsed during which the starch 204 becomes fully plasticized starch 214, the hydraulic cylinder 211 brings the screw assembly 220 forward and uses the screw 208 as a ram for the plasticized starch 214 to be injected through a valve body assembly 250, including a one-way valve 215, a needle valve 223, nozzle 222 and an outlet port 221 into the molding unit 202. The one-way valve 215 prevents the plasticized starch 214 from going back over the helical flutes 216 of the screw 208.

The extruder barrel 217 has heating coils 218 to heat the starch 204 while it is being compressed by the screw 208 into plasticized starch 214. It is desirable for the plasticized starch 214 to be heated at the lowest possible temperature and to be transported with the lowest possible speed of the screw 208. The speed of the screw 208 and the heating of the plasticized starch 214 within the extruder barrel 217 by the steam heating coils 218 control the quality and the output rate of the plasticized starch 214 injected into the molding unit 202. The molding unit 202 holds the mold 206 having capsule shaped cavities 219 into which the plasticized starch 214 is injected and maintained under pressure. Refrigerant cooling conduits 224 encircle the mold 206 so that when the plasticized starch 214 in the mold 206 has cooled and sufficiently solidified, the molding unit 202 opens, the mold 206 separates and the capsule parts 207 are ejected.

Figure 119:
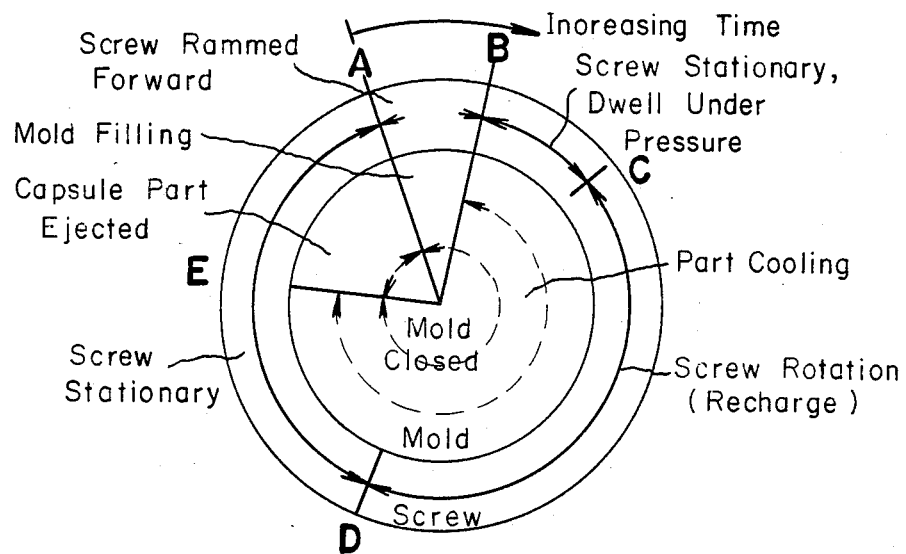
FIG. 119 is a schematic of an injection molding work cycle.

Referring now to FIGS. 118A and 119, which depict the injection molding work cycle for starch 204 containing approximately 20% water by weight. The work cycle of starch 204 generally in the injection molding device 227 of the present invention is as follows:

a. starch 204 is fed into the hopper unit 205 where it is received, stored and maintained under conditions of temperature ranging from ambient to 100° C., pressure ranging from $1-5 \times 10^5$ Newtons per square meter ($N/m^2$) and water content ranging from 5 to 30% by weight of starch;

b. the stored starch 204 is melted under controlled conditions of temperature ranging from 80° to 240° C., water content ranging from 5 to 30% by weight of starch and pressure ranging from 6 to $30 \times 10^7$ $N/m^2$;

c. the molten starch 204 is dissolved in water under controlled conditions of temperature ranging from 80° to 240° C., pressures ranging from 6 to $30 \times 10^7$ $N/m^2$ and water content ranging from 5 to 30% by weight of starch;

d. the dissolved starch 204 is plasticized under controlled conditions of temperature ranging from 80° to 240° C., pressure ranging from 6 to $30 \times 10^7$ $N/m^2$ and water content ranging from 5 to 30% by weight of starch;

e. the plasticized starch 214 is injected into the mold 206 under controlled conditions of temperature above 80° C., at an injection pressure ranging from 6 to $30 \times 10^7$ $N/m^2$ and a clamping force of the mold 206 with a range of approximately 100 to 10,000 Kilo Newton; and f. the capsule-shaped parts 207 are ejected from the plasticized starch 214 within the mold 206.

Beginning at point A of FIG. 119 the screw 208 moves forward and fills the mold 206 with plasticized starch 214 until Point B and maintains the injected plasticized starch 214 under high pressure, during what is called the hold time from point B until Point C of FIG. 119. At Point A the one-way valve 215 at the end of the screw 208 prevents the plasticized starch 214 from flowing back from the cylindrical space in front the screw 208 into the helical flutes of screw 208. During hold time, additional plasticized starch 214 is injected, off-setting contraction due to cooling and solidification of the plasticized starch 214. Later, the outlet port 221, which is a narrow entrance to the molding unit 202 closes, thus isolating the molding unit 202 from the injection unit 201. The plasticized starch 214 within the mold 206 is still at high pressure.

As the plasticized starch 214 cools and solidifies, pressure drops to a level that is high enough to ensure the absence of sinkmarks, but not so high that it becomes difficult to remove the capsule parts 207 from the capsule-shaped cavities 219 within the mold 206. After the outlet port 221 closes, at Point C, screw 208 rotation commences. The plasticized starch 214 is accommodated in the increased cylindrical space in front of the screw 208 created by its backward axial motion until Point D. The flow rate of the plasticized starch 214 is controlled by the speed of the screw 208 and the pressure is controlled by the back pressure (i.e., the hydraulic pressure exerted on the screw assembly 220) which in turn determines the pressure in the plasticized starch 214 in front of the screw 208.

After plasticized starch 214 is generated for the next shot into the mold 206, the screw 208 rotation ceases at Point D. The starch 204 on the stationary screw 208 is held at melt temperature from Points D to E by heat conduction from the heating coils 218 on the extruder barrel 217. Meanwhile, the solidified capsule parts 207 are ejected from the mold 206. Thereafter, the mold 206 closes to accept the next shot of plasticized starch 214. All of these operations are automated and controlled by a microprocessor as hereinafter described.

Referring once again to FIGS. 118, 118A and 119, the injection molding work cycle of FIG. 119 is accomplished on the injection molding device 227 of FIG. 118 by hydraulic and electrical components and the corresponding circuits are controlled by the microprocessor 228 of FIG. 118A.

Through the use of solid-state circuitry and of speed, temperature, limit and pressure switches for the electric and hydraulic systems, the microprocessor 228 of the present invention utilized command signals stored in its memory 251 for the parameters of time, temperature and pressure conditions of Table 1 below for the injection molding work cycle of FIG. 119 to be accomplished by the injection molding device of FIG. 118 for producing starch capsule parts 207.

TABLE 1

Ranges of Time, Temperature and Pressure at the Top of the Screw for the Injection Molding Work Cycle of FIG. 119:

| | POINTS | | | | |
|---|---|---|---|---|---|
| | A<br>−2 | B<br>−2 | C<br>−2 | D<br>−2 | E<br>−2 |
| Time (seconds) | $10^{-1}$ | $10^{-1}$ | $10^{-1}$ | $10^{-1}$ | $10^{-1}$ |
| Temperature (°C.) | 70–100 | 80–240 | 80–190 | 80–240 | 80–240 |
| Pressure | A–B | B–C | C–D | D–E | |

TABLE 1-continued

Ranges of Time, Temperature and Pressure at the Top of the Screw for the Injection Molding Work Cycle of FIG. 119:

| | POINTS | | | | |
|---|---|---|---|---|---|
| | A<br>−2 | B<br>−2 | C<br>−2 | D<br>−2 | E<br>−2 |
| ($10^6$ N/m$^2$) | 60-300 | 60-300 | 1-100 | 1-100 | |

Referring now to FIG. 118A illustrating the combined injection molding device 227 and microprocessor 228 for practicing the method of the present invention:

The combined injection molding device 227 and microprocessor 228 comprises six control circuits of which five are closed-loop, fully analog, and one is on-off. Starting at molding cycle Point A in FIG. 119, the injection molding work cycle operates as follows:

When sufficient plasticized starch 214 has accumulated in front of the screw 208 (microprocessor limit switch controlled) and also when the screw assembly 220 carrying the screw 208, drive 209 and hydraulic motor 211 has been shed far enough backwards against a constant back-pressure as controlled by control circuit 202, limit switch 212 will be actuated by position sensing circuit I4. The two conditions for actuating cylinder 211 are: (1) when the clamping force of the mold is built-up, and (2) limit switch 212 is activated. This rams the barrel 217 together with the nozzle 214 with screw assembly 220 forward for sealing purposes. Sufficient pressure is controlled by control circuit 202 by means of pressure sensor I2. Under these conditions, hydraulic piston 209 rams the screw assembly 220 forward, thus injecting the plasticized starch 214 into the mold 206 when molding cycle Point B of FIG. 119 is reached, and, as controlled by the microprocessor 228, the screw 208 remains for a certain period of time until Point C, stationary in this forward position under high pressure.

From molding cycle Point B of FIG. 119 onwards, the plasticized starch 214 cools down in the mold 206 and the port 221 closes at molding cycle Point C of FIG. 119.

At molding cycle Point C of FIG. 119 the screw 228 starts to rotate again and the hydraulic pressure reduces from holding pressure to back pressure in the hydraulic cylinder 211. This pressure is less than the holding pressure at Point C.

The barrel 217 is kept under constant pressure towards the mold 206 by the pressure in the back position of the hydraulic cylinder 211. This is achieved by means of the control circuit 202 where a proportional hydraulic valve is controlled by a pressure sensor circuit I2.

As the screw 208 rotates, a recharge of starch 204 is made from the hopper 205. During a certain time period and at a defined rotating speed of the screw 208, controlled by control circuit 203, a precise amount of starch 204 is fed into the extruder barrel 217. Control circuit 203 is actuated by speed sensor circuit I3, measuring the rotating speed of the screw 208 and sensing back to a hydraulic proportional flow control valve O3 controlled by control circuit 203, thus assuring a constant rotating speed of the hydraulic motor 210, irrespective of the changing torque resulting from introduction of the starch 204 recharge.

When the load time is completed, the screw 208 rotation is stopped and molding cycle Point D of FIG. 119 is reached. The time from molding cycle Points D to A of FIG. 119 allows for the starch 204 to plasticize completely under controlled temperature conditions as controlled by control circuit 201.

A temperature sensor circuit I1 senses a thyristor heat regulator O1 heating the extruder barrel 217 as directed by control circuit 201.

During the time interval from molding cycle Points B to E on FIG. 119, the mold 206 has cooled down sufficiently so that the finished capsule parts 207 can be ejected from the mold 206.

After ejection of the capsule parts 207, the work cycle returns to Point A of FIG. 119 where a certain volume of plasticized starch 214 has accumulated in front of the screw 208 (sensing circuit I4 is actuated and time has elapsed) so that the work cycle of FIG. 119, can be repeated.

It is important to note the temperature and humidity control loops 5 and 6, for the maintenance of precise water content of the starch 204 in the hopper 205, which is essential for proper operation at the desired speeds.

The microprocessor 228 includes a memory section 251 to store the desired operating parameters; a sensing and signaling section 252 to receive the sensing signals of actual operating conditions, to detect the deviation between the desired and actual operating conditions, and to send signals for adjustment through the actuating section 252 to the thyristors and valves.

Figure 120:
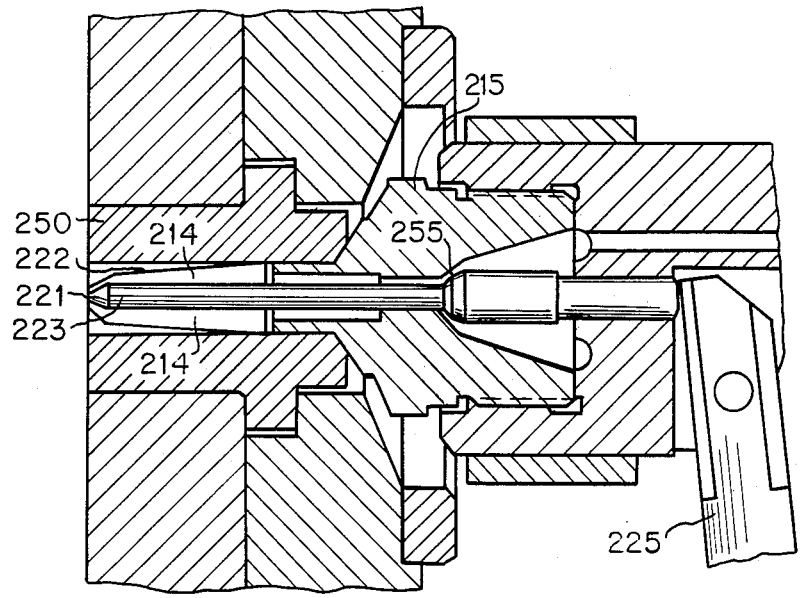
FIG. 120 is an expanded cross-sectional view of the exit end of the injection molding device.

Referring now to FIG. 120 there is shown the valve assembly 250 including the outlet port 221, the nozzle 222, the needle valve 223, and the bearing 215. These elements operate as follows:

At Point A in FIG. 119 the needle valve 223 is retracted from the outlet port 221 when the pressure builds in the starch 214 while the bearing 215 is pressed against the valve body so as to form an inlet opening 255 for plasticized starch 214 into the nozzle 222 which defines a charging chamber for plasticized starch 214. The plasticized starch 214 is injected through nozzle 222 and into the mold 206 during the mold-filling time between Points A and B in FIG. 119. At Point C in FIG. 119 the needle valve 223 is pushed forward so as to close the outlet port 221 during which time between Point C and E in FIG. 119, the inlet of mold 206 is closed and the capsule part 207 in the mold 206 is cooling. The needle valve 223 remains closed between Point E and A in FIG. 119 during which time the capsule part 207 is ejected from the mold 206.

The one-way valve 215 and the needle valve 223 are actuated by a spring-tensioned lever 225 which normally closes both the outlet port 221 and the nozzle 222 until the lever 225 is cam-actuated pursuant to signals from the microprocessor 228.

The thermomechanical properties of starch, i.e. storage and loss shear modules at different temperatures, are strongly dependent on its water content. The capsule molding process of the present invention can be used for starch with a water content preferably within a range of 5 to 30%. The lower limit is defined by the maximum processing temperature of 240° C., which in turn cannot be exceeded in order to avoid degradation. The upper limit is determined by the stickiness and distortion of the finished capsules. It should also be noted that plasticizing is caused by heat and pressure when dealing with thermoplastic materials; however, with starch it is necessary to also have strong shearing forces. The abbreviations in Table 2 below will be used hereinafter in this application:

TABLE 2

Abbreviations for Physical Parameters

| ABBREVIATION | UNIT | DESCRIPTION |
|---|---|---|
| $T_a, P_a$ | °C., N/m$^2$ | Ambient temperature and pressure. |
| $H(T,P)$ | KJoule/Kg$^2$ | Enthalpy of hydrophilic polymer-water system at a given pressure and temperature. |
| $\beta(T,P)$ | m$^2$/N | Compressibility of the hydrophilic polymer at a given temperature and pressure. Its numerical value is the relative volume change due to change of pressure by a unit amount. |
| $\alpha(T,P)$ | (°C.)$^{-1}$ | Volumetric thermal expansion coefficient of the hydrophilic polymer at a given temperature and pressure. Its numerical value is the relative volume change due to change of temperature by a unit amount. |
| $V(g,T,P)$ | Kg/sec$^1$ | Is the flow rate of the hydrophilic polymer at a given temperature and shear deformation rate [sec.$^{-1}$] and pressure. Its numerical value is the volume of a melt leaving the exit cross-sectional area |
| $T_{G1}; T_{G2}$ | °C. | The temperature range of the glass transition of the starch. |
| $T_{M1};$ | °C. | The temperature range for melting the practically crystalline starch. |
| $T_M$ | °C. | The melting temperature of starch. |
| $T_n(t)$ | °C. | The temperature of the starch in the nozzle area of the injection unit. |
| $T_t(t)$ | °C. | The temperature of the starch in the mold. |
| $P_t$ | N/m$^2$ | The pressure of the starch in the mold. |
| $P_n$ | N/m$^2$ | The pressure of the starch in the nozzle area of the mold. |
| X | | The water content of the starch, expressed as the weight fraction of the water - starch system. |

For the control and regulation of the injection molding process (IMP) one needs knowledge of the (1) heat consumption by the melting process:

$$H(T_n, P_n) - H(T_a, P_a)$$

(2) the heating rates of the starch in the injection molding device. To calculate this, one needs the heat conduction number of the starch and the specific material of construction of the barrel which is in contact with the starch. The heating rate and the heat consumption of the starch give the minimum time interval necessary to make the starch ready to inject and the necessary heating power of the injection molding device.

(3) the $T_n$ depends on X of the starch. If the water content of the starch in the mold is too low, the resulting $T_n$ will be too high and cause degradation. A minimum water content of 5% by weight is required to keep $T_n$ below 240° C.

(4) the flow rate $V(g,T,P)$ is strongly dependent as well on the water content of the starch. To speed up the IMP we need a high flow rate $V(g,T,P)$ which can be achieved by starch with a higher water content.

The upper limit of the water content is defined by the stickiness and mechanical failure of the capsules; a water content of 0.30 cannot be generally exceeded.

The starch in the mold will reduce its volume due to the temperature change $T_t - T_a$. This would result in voids and diminution of size of the capsule, which therefore would be of unacceptable quality. It is an important requirement in capsule making that the dimensional deviations are less than 1%. To compensate for shrinking by the temperature change, the mold must be filled at a distinct pressure Pn. This filling pressure is determined by the quantities (T,P) and K(T,P). The injection pressure depends again on $T_n$ which, as was shown already, is in turn strongly dependent on X.

Figure 121:
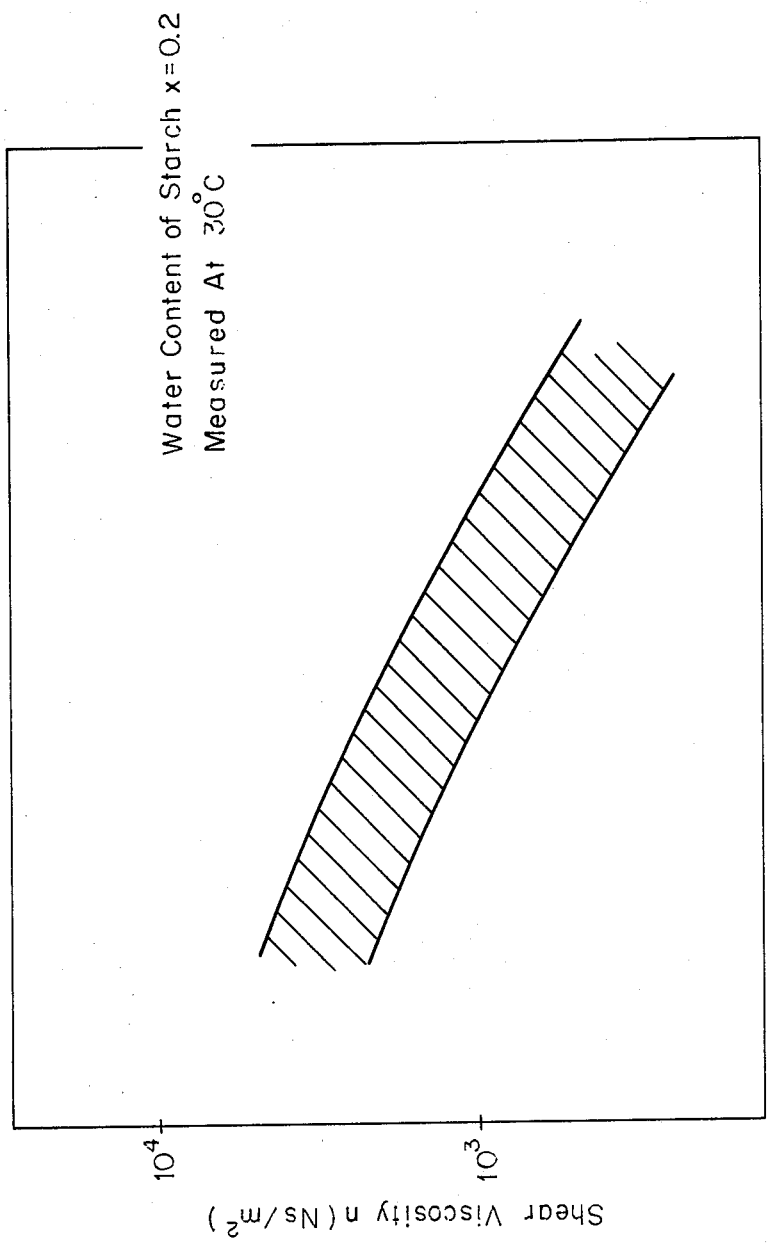
FIG. 121 is a graph of the dependence of shear viscosity of starch within the pertinent ranges of the shear rate for the present invention.

Referring now to FIG. 121, the shear rate dependent shear viscosity of starch at 130 degrees C. is shown for starch with a water content (X) of 0.2.

Figure 122:
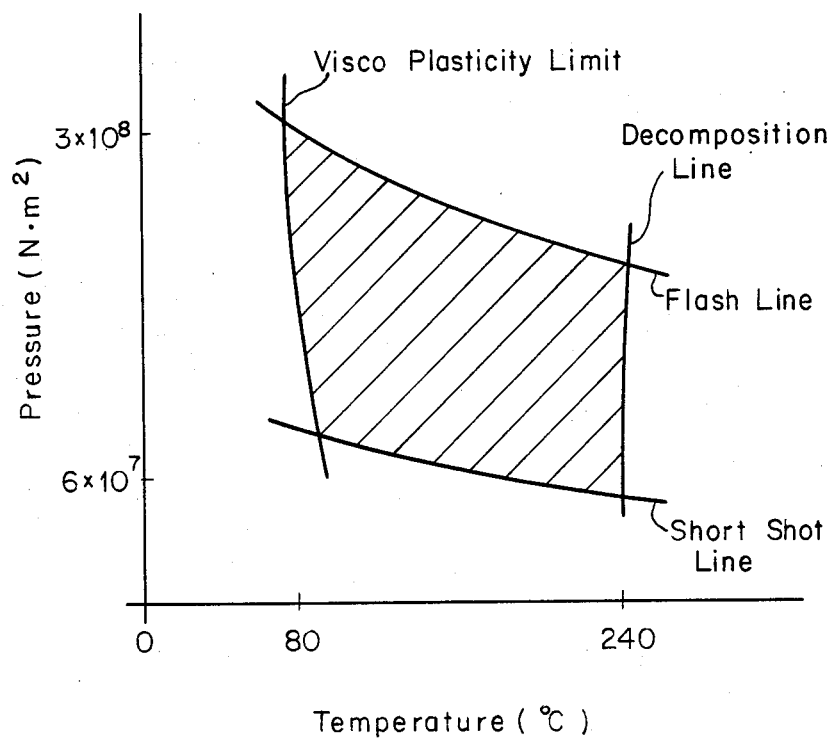
FIG. 122 is a graph of molding area for starch within the ranges of temperature and pressure of starch for the present invention.

Referring now to FIG. 122, the molding area diagram for starch with a water content of 0.024, during injection molding the plasticized starch is discontinuously extruded and immediately cooled in a mold of the desired shape of the capsule part. Moldability depends on the starch properties and the process conditions, of which the thermo-mechanical properties of the starch as well as the geometry and the temperature and pressure conditions of the mold are the most important. In the molding area diagram of FIG. 111 the limits of pressure and temperature are indicated for the processing of starch in the combined injection molder-microprocessor of the present invention. The maximum temperature of 240° C. is determined by visible degradation of the starch above that limit. The lower temperature limit of 80° C. was determined by the development of too high viscosity and melt elasticity in the preferred water content range X: 0.05 to 0.30. The higher pressure limits of $3 \times 10^8$ N×m$^{-2}$ are given by the start of flashing when the melted starch flows in a gap between the various metal dies which make up the molds, thus creating thin webs attached to the molded starch capsule parts at the separating lines. The lower pressure limits of about $6 \times 10^7$ N×m$^{-2}$ are determined by short shots, when the mold cannot be completely filled by the starch. Shown below in Table 3 are the working parameters for the injection molding process using the starch composition of the present invention.

TABLE 3

WORKING PARAMETERS FOR INJECTION MOLDING PROCESS

| | |
|---|---|
| Density | $1.5 \times 10^3$ kg/m$^3$ |
| Crystallinity | 20 to 70% |
| $H(T_n,P_n) - H(T_a,P_a)$ | 63 KJoule/kg |
| Net heating performance | $6.3 \times 10^2$ KJoule |

TABLE 3-continued
WORKING PARAMETERS FOR INJECTION MOLDING PROCESS

| | |
|---|---|
| for 10 kgs. melt/h (corresponding to $10^6$ capsules/h) ($T_a, P_a$) | $3.1 \times 10^{-4}$ (°C.)$^{-1}$ |
| Contraction due to crystallization | negligible |
| Critical shear deformation rate | $10^4$–$10^6$ sec$^{-1}$ |

Figure 123:
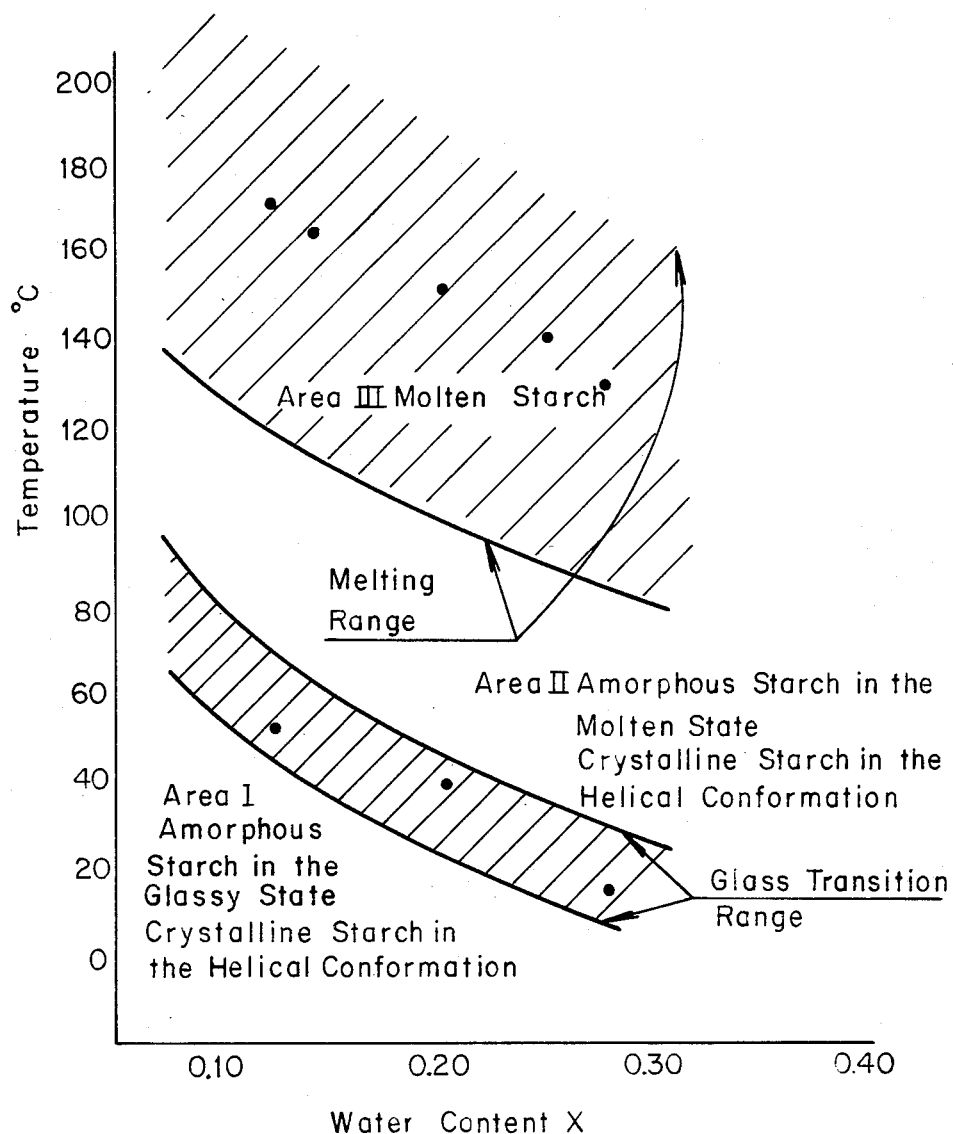
FIG. 123 is a graph of the dependence of the glass transition temperature range and melting temperature range on the pertinent water content ranges of starch.

Referring now to FIG. 123, the glass transition range and the melting temperature range is shown as a function of the composition of the starch-water system. The melting range is very high (over 100° C.) in comparison with the melting range of, for example, gelatin, which is about 20° C. At temperatures below the glass transition range, ordinary starch, as available commercially, is a partially crystalline polymer containing approximately 30–100% amorphous and approximately 0–70% crystalline parts by volume. By raising the temperature of the starch at a distinct water content the starch passes through the glass transition range.

Referring again to FIG. 118 said heating process of the starch will take place within the extruder barrel 217. Referring again to FIG. 119 said heating process of the starch will take place during the entire injection molding work cycle. The area in FIG. 123 between the glass transition range and the melting range is called area II. In area III we find crystalline starch and a starch melt. The glass-transition is not a thermodynamic transition range of any order but is characterized by a change of the molecular movement of the starch molecules and by a change of the bulk storage module of the amorphous starch by several orders of magnitude. By passing from area II to area I in FIG. 123 the translational movements of the starch molecules or those of large parts of said molecules will be frozen in the glass transition temperature range and this is reflected by a change, in the specific heat ($C_p$) and the volumetric thermal expansion coefficient in temperature range. By passing from area II to area III due to crossing the melting range of the crystalline starch, the helically ordered part of the starch will melt. Referring to FIG. 118 said heating process of the starch will take place within the extruder barrel 217. Referring again to FIG. 119, said heating process of the starch will take place during the entire injection molding work cycle. Said helix-coil transition is a true thermodynamic of the first order and is an endothermic process. Said transitions can be detected by scanning calorimetry or by measurement of the change of the linear viscoelastic bulk storage module due to changes in the temperature.

Figure 124:
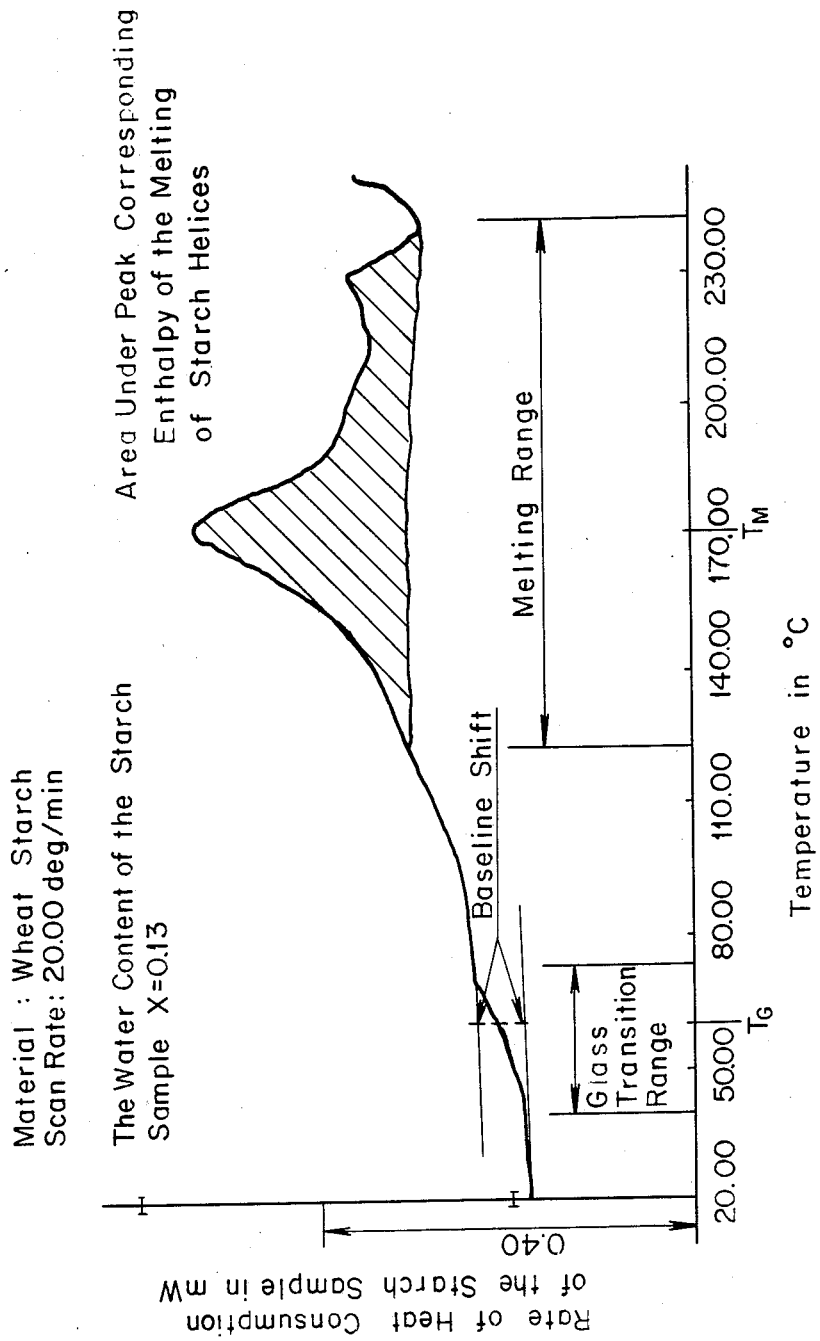
FIG. 124 is a graph of the dependence of a differential calorimeter scan in which the heat consumption rate of the starch is plotted for the pertinent temperature range of the present invention.

A typical plot of a temperature scan with a differential calorimeter is shown in FIG. 124. On the ordinate is plotted the velocity of the heat consumed by the sample relative to a reference (empty sample holder). The velocity of heat consumption of the sample is due to the change of the temperature of the starch sample, and said temperature is plotted on the abscissa as degrees of Celsius. The base line shift on said plot corresponds to the glass transition and the peak to the melting or to the helix-coil transition. The linear viscoelastic bulk storage module E can be measured even at small sinusoidal shear deformation of the starch sample.

Referring again to FIG 118 the heating of the starch 204 to a temperature higher than $T_M$ takes place in the forward part of the extruder barrel 217. Said heating process will be maintained not only by the heating coils 218 but to a great degree by the internal friction during the screw rotation and the injection process due to the high deformational rates. It was found that the reversible elastic deformation of the injection molded starch 214, after opening the mold 206, is negligible if the temperature of the plasticized starch 214 during the injection process is higher than $T_M$. Otherwise the molding sequence would drop by at least an order of magnitude.

Referring again to FIG. 119, the necessary cooling period for the plasticized starch in the molds—to prevent any reversible elastic deformation of said starch—will take place between points B and E of the working cycle. A restriction of the molding sequence to low speed coupled with keeping the starch in the mold for an extended period is undersirable for two reasons: low output of the product and loss of water content by the starch in the extruder. At the elevated injection temperature there is always a movement of water from the hot to the cold starch in the extruder barrel. Said water transport can be compensated for due to the transport of the starch by the screw in the opposite direction.

Figure 125:
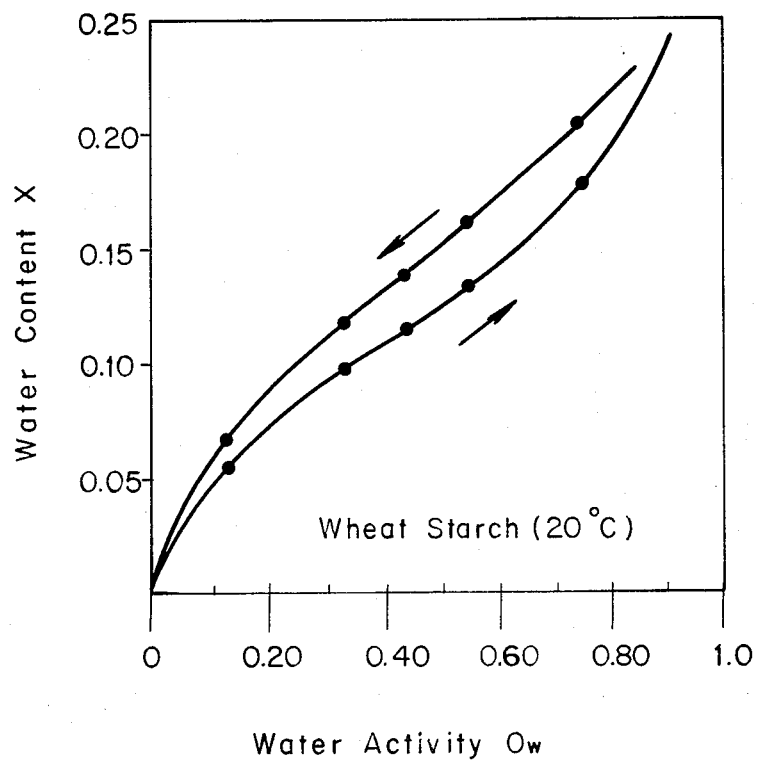
FIG. 125 is a graph of dependence of the equilibrium water content of the starch in the water activity program.

Referring again to FIG. 118, the transport of starch 204 will be maintained by screw 208. Referring again to FIG. 119, the transport of starch will take place between points C and D of the working cycle. To build up a stationary water content of the starch in the melting area of the extruder barrel, it is necessary to work at an injection sequence which is short. To establish a constant and high enough water content of the starch in the extruder barrel, it is further necessary to use starch with the proper shape of the sorption isotherm. (See FIG. 125) The constant water content of the starch in the extruder barrel is necessary due to the maintenance of constant production conditions. The water content of the starch during the injection must fulfill the following condition: X higher than 0.05. Otherwise $T_M$ is also higher than 240° C. and this is undersirable due to the resultant degradation of the starch.

In the procedure of branching and crosslinking of starch, it is important to add the crosslinking agents listed above, especially the covalent crosslinking agents, shortly before the injection of the molten starch 214.

Referring again to FIG. 118, an aqueous solution of crosslinking agents is injected in front of a mixing system placed between barrel 217 and nozzle 215. Referring now to FIG 120, this device is integrated in the valve body 250. For example, the crosslinking reaction mainly occurs during the injection cycle and the time after ejection of the capsule. By the above described technology on branching and crosslinking there is no disadvantage, i.e., no changing of the thermo-mechanical properties of the starch polymers, during the melting and solution process.

The starch compositions are extruded and injected under the following conditions given in Table 4 below:

TABLE 4
Injection and Molding Conditions for Starch Injection Unit

| | | | | | |
|---|---|---|---|---|---|
| Screw diameter mm | | 24 | 28 | 32 | 18 |
| Injection pressure $10^8$ N/m$^2$ | | 2.2 | 1.68 | 1.6 | — |
| Calculated injection cm$^3$ | | 38 | 51.7 | 67 | 21.3 |
| Effective screw length L:D | | 18.8 | 16.1 | 13 | 18 |
| Plasticising capacity kg/h(max.) | (1a) | 13.5 | 21.2 | 21 | — |

TABLE 4-continued

Injection and Molding Conditions for Starch Injection Unit

| (PS) | (11a) | 9.2 | 14.5 | 15 | — |
|---|---|---|---|---|---|
| | (1b) | 23.6 | 34 | 36 | — |
| | (11b) | 17.5 | 27 | 27 | — |
| Screw Stroke mm(max.) | | 84 | 84 | 84 | 84 |
| Injection capacity kW | | 30 | 30 | 30 | — |
| Injection velocity $10^3$mm/s(max.) | | 2 | 2 | 2 | 2 |
| Nozzle contact force kN | | 41.2 | 41.2 | 41.2 | 41.2 |
| Screw rotating speed min$^{-1}$ | | Var. (1a) | 20 | −80 | — |
| | | (11a) | 20 | −17 | — |
| | | Var. (1b) | 20 | −60 | — |
| | | (11b) | 20 | −40 | — |
| Number of heating zones | 5 | 5 | 5 | 5 | 5 |
| Installed heating capacity kW | | 6.1 | 6.1 | 6 | — |
| Molding Unit | | | | | |
| Clamping force kN | | | | 60 | |

EXAMPLES

The scope of the invention is further described in connection with the following examples which are set out for the sole purpose of illustrating the preferred embodiments of the invention and which are not to be construed as limiting in any way the scope of the invention.

EXAMPLE 1

A wheat starch containing 20.6% of water was injection molded to a capsule body at 140° C. and a pressure of $2 \times 10^8$ N/cm$^2$ as well as to a capsule at the same conditions, the cap and body having the form as disclosed in FIG. 4. An excellent locking capsule was obtained with a smooth outer surface.

EXAMPLE 2

Example 1 was repeated using the form of FIG. 8. The joining surfaces of the cap and body parts where moistened with water, which resulted in excellent sealing properties.

EXAMPLE 3

Figure 43:
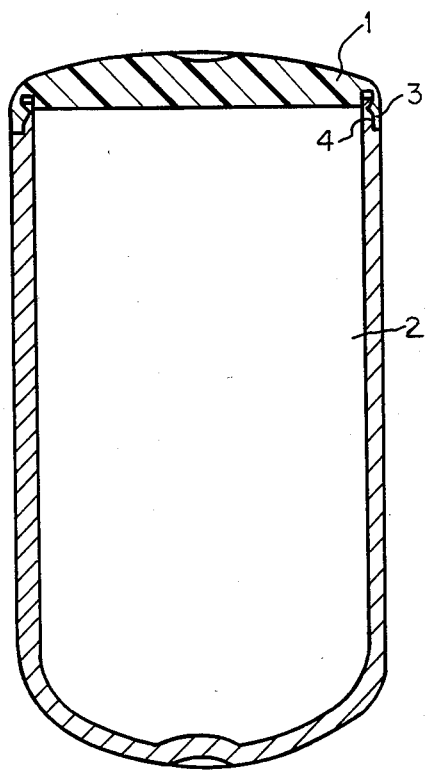
Figure 42A:
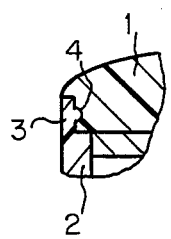
FIGS. 42(A) and 43(A) are partial cross-sectional views of the capsules of FIGS. 42 and 43, respectively.
Figure 43A:
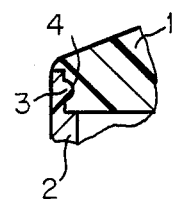

Example 1 was repeated using the capsule of FIG. 43, having the name CAPSUGEL embossed on the cap, with highly satisfactory results with respect to air-entrapment and sealing quality. The depth of the embossed letters was 0.03 mm which was sufficient for clean reading. The same result was obtained with debossing.

In addition, to test the method and apparatus as described above, batches of commercially available native starch with different water contents and extenders were prepared and conditioned and then tested in an injection molding machine at different working conditions. Referring to FIG. 119, the cycle times of the injection molding-microprocessor apparatus were as follows:

| Cycle Points | Times |
|---|---|
| A–B | 1 second, variable, depending on temperature |
| B–C | 1 second |
| C–D | 1 second |
| D–E | variable, depending on temperature |
| E–A | 1 second |

Pressure in the nozzle: $2 \times 10^8$ N/m$^2$
Temperatures along screw: variable, see Examples.

In the Examples, the following abbreviations are used:
$T_b$ temperature at beginning of screw (°C.)
$T_m$ temperature at middle of screw (°C.)
$T_e$ temperature at end of screw (°C.)
$T_n$ temperature at nozzle (°C.)
LFV linear flow velocity (mm/second)
L flow length (cm)
D film thickness (cm)
bw by weight Acceptable starch capsules were processed according to the starch compositions and the working conditions tabulated in the Examples below:

EXAMPLE 4

Starch composition:
Wheat starch, gelatin 150B, water: 8.2% bw, 73.8% bw, 18% bw
Working conditions:

| number | $T_b$ | $T_m$ | $T_e$ | $T_n$ | $\frac{L}{D}$ | LFV |
|---|---|---|---|---|---|---|
| 76S | 125 | 130 | 140 | 140 | 66 | 1000 |

EXAMPLE 5

Starch composition:
Wheat starch, gelatin 150B, water: 41% bw, 41% bw, 18% bw
Working conditions:

| number | $T_b$ | $T_m$ | $T_e$ | $T_n$ | $\frac{L}{D}$ | LFV |
|---|---|---|---|---|---|---|
| 126S | 125 | 135 | 140 | 140 | 66 | 820 |

EXAMPLE 6

Starch composition:
Wheat starch, gelatin 150B, water: 67.6% bw, 24.6% bw, 15.8% bw
Working conditions:

| number | $T_b$ | $T_m$ | $T_e$ | $T_n$ | $\frac{L}{D}$ | LFV |
|---|---|---|---|---|---|---|
| 298S | 125 | 135 | 140 | 140 | 66 | 1200 |

EXAMPLE 7

Starch composition:
Wheat starch, water: 79.4% bw, 20.6% bw
Working conditions:

| number | $T_b$ | $T_m$ | $T_e$ | $T_n$ | $\frac{L}{D}$ | LFV |
|---|---|---|---|---|---|---|
| 305S | 115 | 130 | 140 | 140 | 66 | 820 |

EXAMPLE 8

Starch composition:
Wheat starch, water, erythrosine: 78.32% bw, 21.6% bw, 0.0078% bw
Working conditions:

| number | $T_b$ | $T_m$ | $T_e$ | $T_n$ | $\frac{L}{D}$ | LFV |
|---|---|---|---|---|---|---|
| 349S | 110 | 125 | 135 | 135 | 66 | 1000 |

EXAMPLE 9

Starch composition:
Wheat starch, HPMCP, lubricants+plasticizers, water: 9.2% bw, 74.1% bw, 5.1% bw, 7.5% bw
Working conditions:

| number | $T_b$ | $T_m$ | $T_e$ | $T_n$ | $\frac{L}{D}$ | LFV |
|---|---|---|---|---|---|---|
| 349S | 110 | 125 | 135 | 135 | 66 | 1000 |

This starch composition was used to produce an enteric capsule

EXAMPLE 10

Starch composition:
Wheat starch, water: 78.5% bw, 21.5% bw
Working conditions:

| number | $T_b$ | $T_m$ | $T_e$ | $T_n$ | $\frac{L}{D}$ | LFV |
|---|---|---|---|---|---|---|
| 400S | 130 | 150 | 160 | 160 | 66 | 820 |
| 404S | 110 | 115 | 125 | 125 | 66 | 820 |

EXAMPLE 11

Starch composition:
Wheat starch, water: 87.3% bw, 12.7% bw
Working conditions:

| number | $T_b$ | $T_m$ | $T_e$ | $T_n$ | $\frac{L}{D}$ | LFV |
|---|---|---|---|---|---|---|
| 405S | 150 | 160 | 170 | 170 | 66 | 820 |

EXAMPLE 12

Starch composition:
Wheat starch, Calcium-stearate, water: 76.8% bw, 3% bw, 20.2% bw
Working conditions:

| number | $T_b$ | $T_m$ | $T_e$ | $T_n$ | $\frac{L}{D}$ | LFV |
|---|---|---|---|---|---|---|
| 411S | 100 | 110 | 135 | 135 | 66 | 880 |
| 413S | 130 | 140 | 160 | 160 | 66 | 820 |

EXAMPLE 13

Starch composition:
Wheat starch, glycerine, water: 77.2% bw, 3% bw, 19.8% bw
Working conditions:

| number | $T_b$ | $T_m$ | $T_e$ | $T_n$ | $\frac{L}{D}$ | LFV |
|---|---|---|---|---|---|---|
| 410S | 100 | 110 | 130 | 130 | 66 | 860 |
| 414S | 130 | 140 | 160 | 160 | 66 | 840 |

EXAMPLE 14

Starch composition:
Wheat starch, Polyethylene-glycol (10,000 m.w., water: 72.5% bw, 3% bw, 22.5% bw, 2% bw
Working conditions:

| number | $T_b$ | $T_m$ | $T_e$ | $T_n$ | $\frac{L}{D}$ | LFV |
|---|---|---|---|---|---|---|
| 412S | 100 | 110 | 130 | 130 | 66 | 840 |
| 415S | 130 | 140 | 160 | 160 | 66 | 840 |

EXAMPLE 15

Starch composition:
Potato starch, water: 80.7% bw, 19.3% bw
Working conditions:

| number | $T_b$ | $T_m$ | $T_e$ | $T_n$ | $\frac{L}{D}$ | LFV |
|---|---|---|---|---|---|---|
| 417S | 100 | 110 | 130 | 130 | 66 | 840 |

EXAMPLE 16

This example demonstrated the dependence of the capsules' disintegration properties on their amylase content. For these tests, the capsules were filled with lactose.

| starch composition | working conditions (°C.) | | | | | | disintegration property of the capsules |
|---|---|---|---|---|---|---|---|
| | $T_b$ | $T_m$ | $T_e$ | $T_n$ | $\frac{L}{D}$ | LFV | |
| maize starch (about 20% amylose) | 110, | 120, | 140, | 140, | 66 | 840 | flocuation in water of 36° C., disintegration within 30 min. |
| maize starch (65% amylose) 80% bw, water 20% bw | 110, | 120, | 140, | 140, | 66 | 840 | no opening in water of 36° C. within 30 min. |
| maize starch (0% amylose, 100% amylopectin) 79.2 bw, water 20.8% bw | 110, | 120, | 140, | 140, | 66 | 836 | disintegration in water of 36° C. disintegration within 30 min. |

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed invention are considered to be within the purview and scope of this invention and the following claims.

What is claimed is:

1. A method for making a starch/water pharmaceutical capsule which comprises:
   (a) providing a composition consisting essentially of starch/water mixture having a water content in the range of about 5 to 30% by weight based on the weight of starch and water;
   (b) heating said starch/water composition at elevated pressure above its glass transition temperature and melting point while maintaining said water content, to form a melt;
   (c) further heating and plasticizing said molten starch-water composition to dissolve the starch in the water to form an essentially molecularly dispersed solution of the melt;
   (d) injection molding the plasticized starch at an elevated pressure and temperature into a mold;
   (e) forming the capsule into a multichambered configuration;
   (f) ejecting the molded capsule from the mold.

2. The method of claims 1 which further comprises adding at least one of a lubricant, a dyestuff, a pigment, a coloring agent, or mixtures thereof, to the composition.

3. The method of claim 1 wherein the composition is plasticized at a temperature of between about 80° C. and 240° C.

4. The method of claim 3 wherein the composition is plasticized at a temperature of between about 110° and 180° C.

5. The method of claim 1 wherein starch is formed into a melt by extrusion.

6. The process of claim 5 wherein extrusion occurs at a pressure between about 6 times $10^7$, N/m$^2$ and 3 times $10^8$, N/m$^2$.

* * * * *